US011390852B2

(12) United States Patent
Ghaedi et al.

(10) Patent No.: US 11,390,852 B2
(45) Date of Patent: Jul. 19, 2022

(54) COMPOSITIONS AND METHODS OF PREPARING AIRWAY CELLS

(71) Applicant: Yale University, New Haven, CT (US)

(72) Inventors: Mahboobe Ghaedi, New Haven, CT (US); Laura Niklason, Greenwich, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/100,978

(22) PCT Filed: Jan. 14, 2015

(86) PCT No.: PCT/US2015/011284
§ 371 (c)(1),
(2) Date: Jun. 1, 2016

(87) PCT Pub. No.: WO2015/108893
PCT Pub. Date: Jul. 23, 2015

(65) Prior Publication Data
US 2016/0312190 A1    Oct. 27, 2016

Related U.S. Application Data

(60) Provisional application No. 61/927,097, filed on Jan. 14, 2014.

(51) Int. Cl.
*C12N 5/071* (2010.01)
*A61K 35/36* (2015.01)

(52) U.S. Cl.
CPC ............ *C12N 5/0688* (2013.01); *A61K 35/36* (2013.01); *C12N 5/0689* (2013.01); *C12N 2500/99* (2013.01); *C12N 2501/115* (2013.01); *C12N 2501/15* (2013.01); *C12N 2501/155* (2013.01); *C12N 2501/415* (2013.01); *C12N 2506/45* (2013.01)

(58) Field of Classification Search
CPC ..... A61K 35/36; A61P 11/00; C12N 2500/99; C12N 2501/115; C12N 2501/15; C12N 2501/155; C12N 2501/415; C12N 2506/45; C12N 5/0688; C12N 5/0689
See application file for complete search history.

(56) References Cited

FOREIGN PATENT DOCUMENTS

| JP | 2012516699 A | 7/2012 |
|---|---|---|
| JP | 6702876 B2 | 5/2020 |
| WO | 2006128025 A2 | 11/2006 |
| WO | 2010091188 A1 | 8/2010 |
| WO | 2013106677 A1 | 7/2013 |
| WO | 2015108893 A1 | 7/2015 |

OTHER PUBLICATIONS

PCT International Search Report and Written Opinion for PCT International Application No. PCT/US2015/011284 dated Jun. 3, 2015.
Chun, et al., "Applications of patient-specific induced pluripotent stem cells; focused on disease modeling, drug screening and therapeutic potentials for liver disease", Int J Biol Sci. 6(7), Dec. 14, 2010, 796-805.
Flotte, et al., "Viral vector-mediated and cell-based therapies for treatment of cystic fibrosis", Mol Ther. 15(2), Feb. 2007, 229-241.
Inoue, et al., "The use of induced pluripotent stem cells in drug development", Clin Pharmacol Ther. 89(5), May 2011, 655-661.
Kerem, et al., "Identification of the cystic fibrosis gene: genetic analysis", Science 245(4922), Sep. 8, 1989, 1073-1080.
Kim Chiaw, et al., "Insights into the mechanisms underlying CFTR channel activity, the molecular basis for cystic fibrosis and strategies for therapy", Essays Biochem. 50(1), Sep. 7, 2011, 233-248.
Leblond, et al., "Developing cell therapy techniques for respiratory disease: intratracheal delivery of genetically engineered stem cells in a murine model of airway injury", Hum Gene Ther. 20(11), Nov. 2009, 1329-1343.
Onder, et al., "New lessons learned from disease modeling with induced pluripotent stem cells", Curr Opin Genet Dev. 22(5), Oct. 2012, 500-508.
Petersen, et al., "Bioreactor for the long-term culture of lung tissue", Cell Transplant. 20(7), 2011, 1117-1126.
Rana, et al., "Characterization of human-induced pluripotent stem cell-derived cardiomyocytes: bioenergetics and utilization in safety screening", Toxicol Sci. 130(1), Nov. 2012, 117-131.
Riordan, et al., "Identification of the cystic fibrosis gene: cloning and characterization of complementary DNA", Science 245(4922), Sep. 8, 1989, 1066-1073.
Rommens, et al., "Identification of the cystic fibrosis gene: chromosome walking and jumping", Science 245(4922), Sep. 8, 1989, 1059-1065.
Rowntree, et al., "Induced pluripotent stem cells: opportunities as research and development tools in 21st century drug discovery", Regen Med. 5(4), Jul. 2010, 557-568.
Serrano-Mollar, et al., "Intratracheal transplantation of alveolar type II cells reverses bleomycin-induced lung fibrosis", Am J Respir Crit Care Med. 176(12), Dec. 15, 2007, 1261-1268.
Somers, et al., "Generation of transgene-free lung disease-specific human iPS cells using a single excisable lentiviral stem cell cassette", Stem Cells 28(10), Oct. 2010, 1728-1740.
Sueblinvong, et al., "Novel therapies for the treatment of cystic fibrosis: new developments in gene and stem cell therapy", Clin Chest Med. 28(2), Jun. 2007, 361-379.

(Continued)

*Primary Examiner* — Blaine Lankford
(74) *Attorney, Agent, or Firm* — Saul Ewing Arnstein & Lehr LLP; Kathryn Doyle

(57) ABSTRACT

The present invention provides compositions and methods of preparing airway cells. In one aspect, an epithelial airway cell derived from an induced pluripotent stem (iPS) cell characterized by expression of airway cell surface markers and an ability to proliferate is described. In another aspect, methods of differentiating an iPS into an epithelial airway cell is provided. Engineered lungs, methods of making such engineered lungs comprising the epithelial airway cells and treating respiratory disorders are also disclosed.

7 Claims, 31 Drawing Sheets

(56) References Cited

OTHER PUBLICATIONS

Tsui, et al., "The cystic fibrosis gene: a molecular genetic perspective", Cold Spring Harb Perspect Med. 3(2), Feb. 1, 2013, a009472.
Walia, et al., "Induced pluripotent stem cells: fundamentals and applications of the reprogramming process and its ramifications on regenerative medicine", Stem Cell Rev. 8(1), Mar. 2012, 100-115.
Wang, et al., "Transplantation of human embryonic stem cell-derived alveolar epithelial type II cells abrogates acute lung injury in mice", Mol Ther. 18(3), Mar. 2010, 625-634.
Wong, et al., "Directed differentiation of human pluripotent stem cells into mature airway epithelia expressing functional CFTR protein", Nat Biotechnol. 30(9), Sep. 2012, 876-882.
Zhang, et al., "iPSCs and small molecules: a reciprocal effort towards better approaches for drug discovery", Acta Pharmacol Sin. 34(6), Jun. 2013, 765-776.
European Search Report for European Patent Application No. 15737803.5 dated Jul. 4, 2017.
Ghaedi, et al., "Human iPS cell-derived alveolar epithelium repopulates lung extracellular matrix", The Journal of Clinical Investigation 123(11), Nov. 2013, 4950-4962.
Ghaedi, et al., "Human Pluripotent Stem Cells (iPSC) Generation, Culture, and Differentiation to Lung Progenitor Cells", Database Medline U.S. National Library of Medicine (NLM), Bethesda, MD. Database Accession No. NLM27628133, 2016, Abstract Only.
Huang, et al., "Efficient generation of lung and airway epithelial cells from human pluripotent stem cells", Nat Biotechnol. 32(1), 2014, 84-91.
Mou, et al., "Generation of multipotent lung and airway progenitors from mouse ESCs and patient-specific cystic Fibrosis iPSCs", Cell Stem Cell. 10(4), Apr. 2012, 385-397.
Park, et al., "Sox17 influences the differentiation of respiratory epithelial cells", Dev Biol. 294(1), 2006, 192-202.
Yoshie, et al., "Generation of airway epithelial cells with native characteristics from mouse induced pluripotent stem cells", Cell Tissue Res. 364(2), 2016, 319-330.
Wagner Darcy E. et al: "Can stem cells be used to generate new lungs? Ex vivo lung bioengineering with decellularized whole lung scaffolds : Ex vivo lung bioengineering", Respiro Logy, vol. 18, No. 6, Aug. 1, 2013 (Aug. 8, 2013), pp. 895-911.
Extended European Search Report for European Patent Application No. 21186095.2 dated Oct. 27, 2021, 13 pages.

FIG. 6A
FIG. 6C
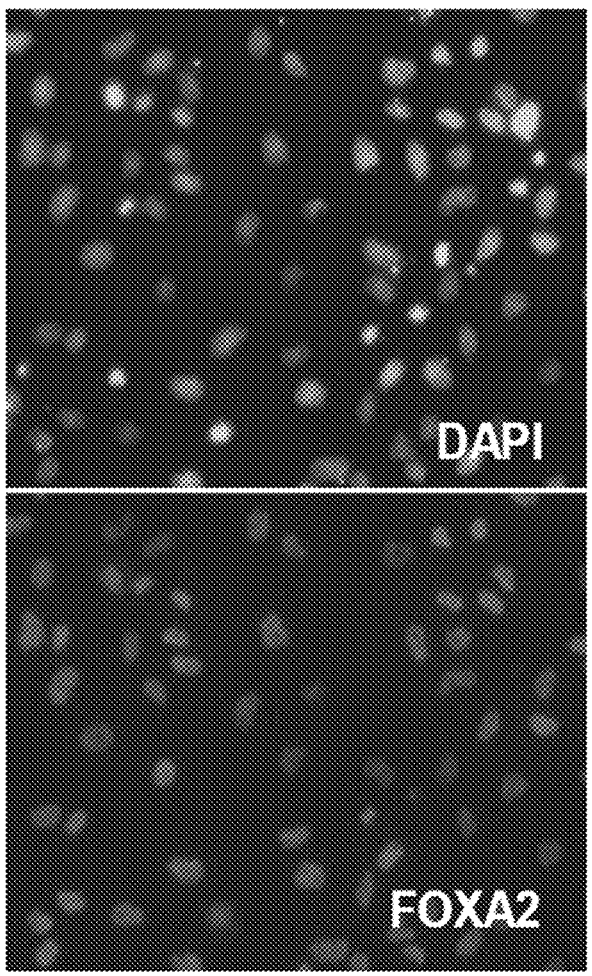
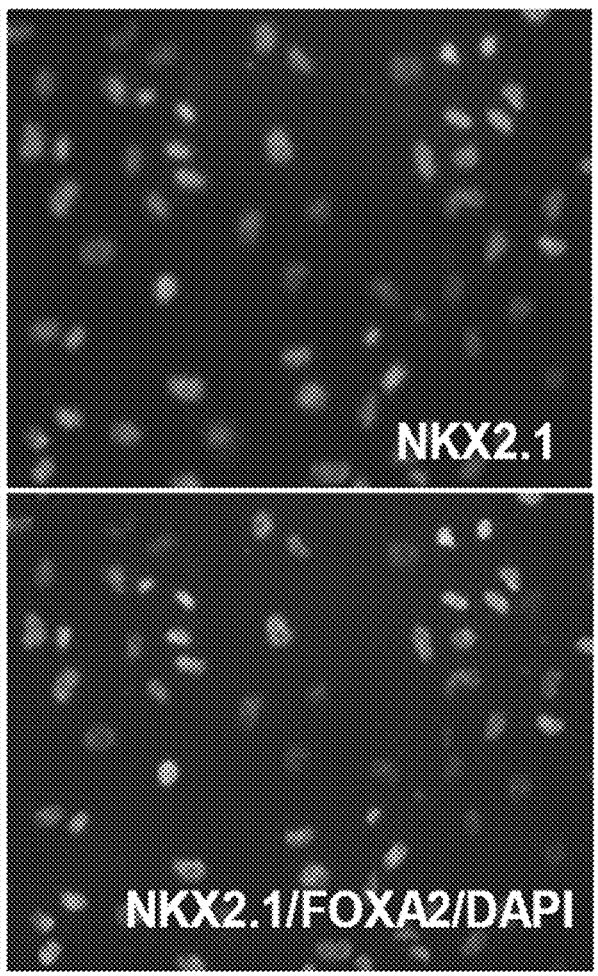
FIG. 6B
FIG. 6D

FIG. 7A
FIG. 7C
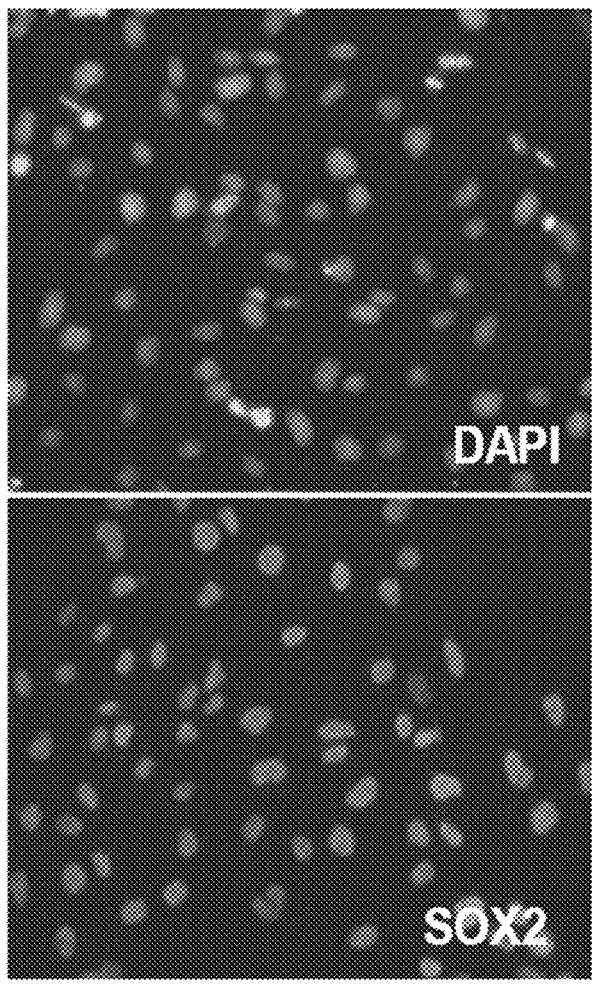
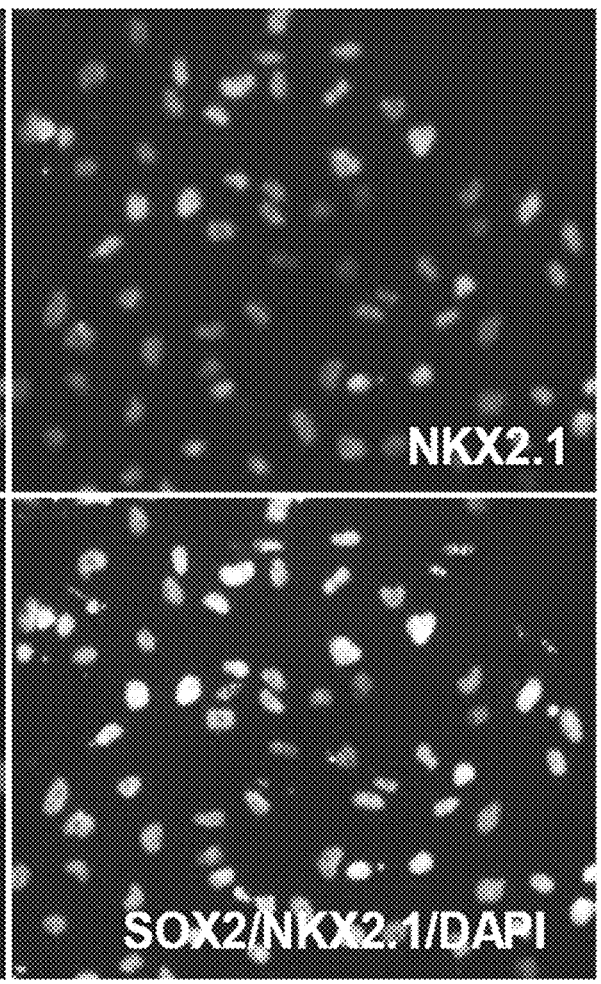
FIG. 7B
FIG. 7D

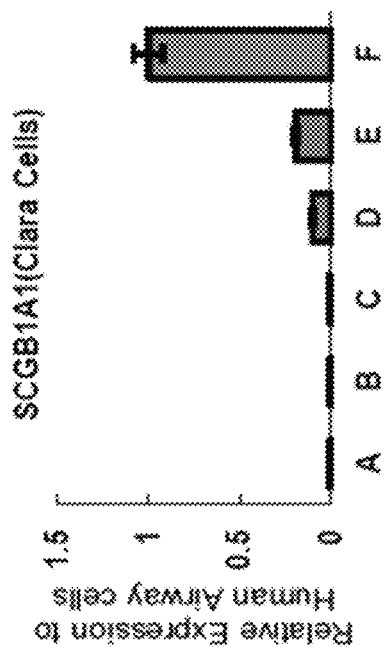
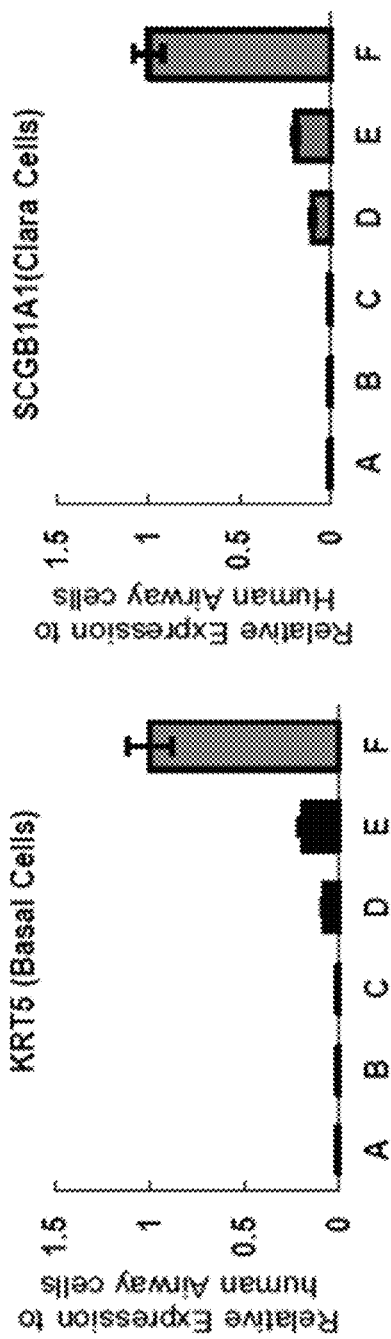
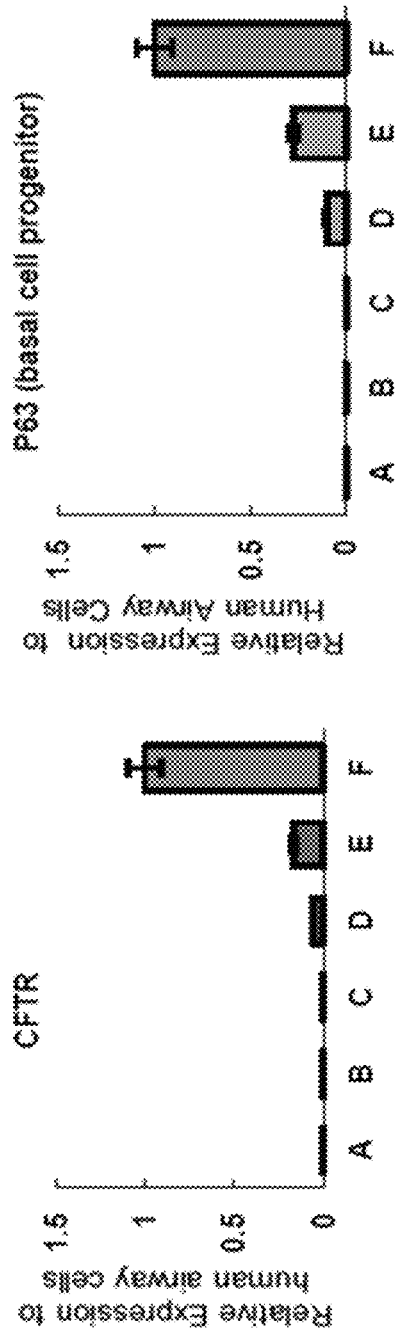
FIG. 10B  FIG. 10D
FIG. 10C  FIG. 10E

FIG. 12E
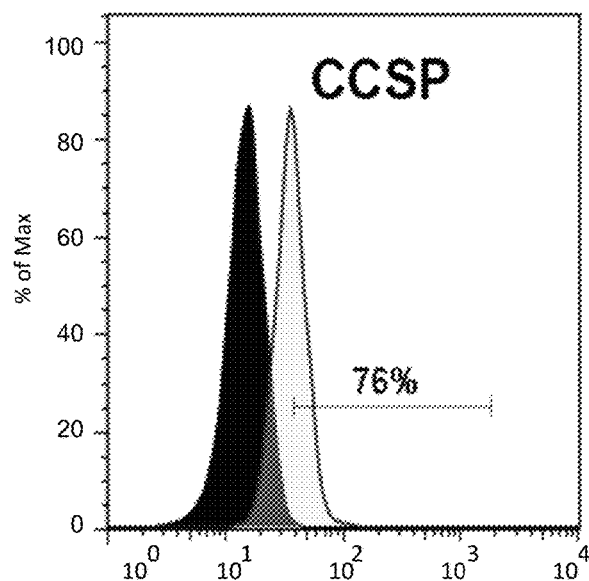
FIG. 12F
FIG. 12G
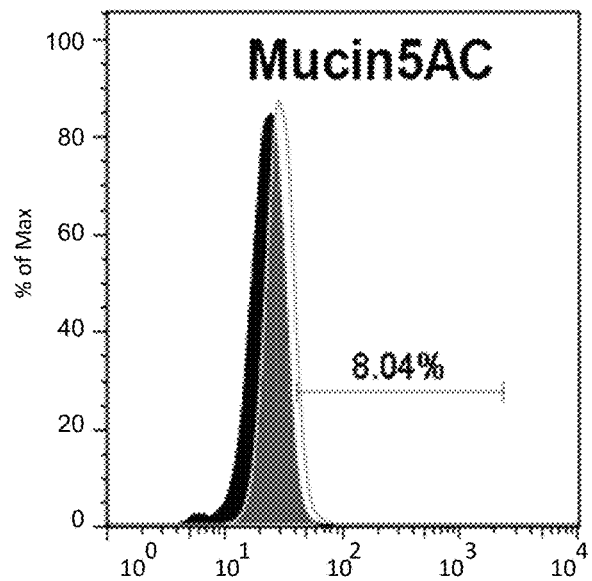
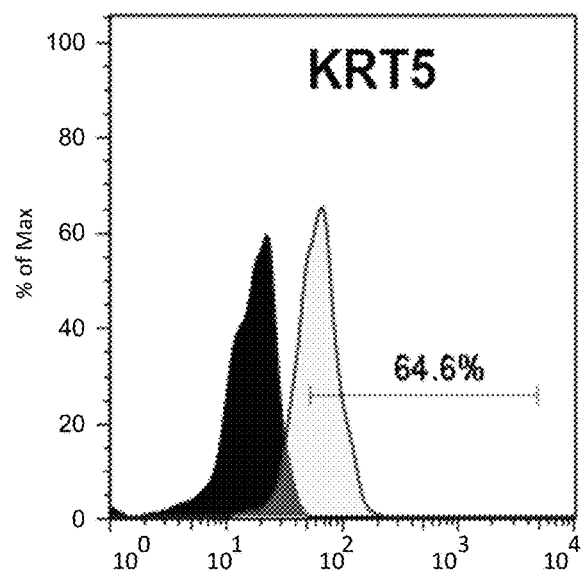
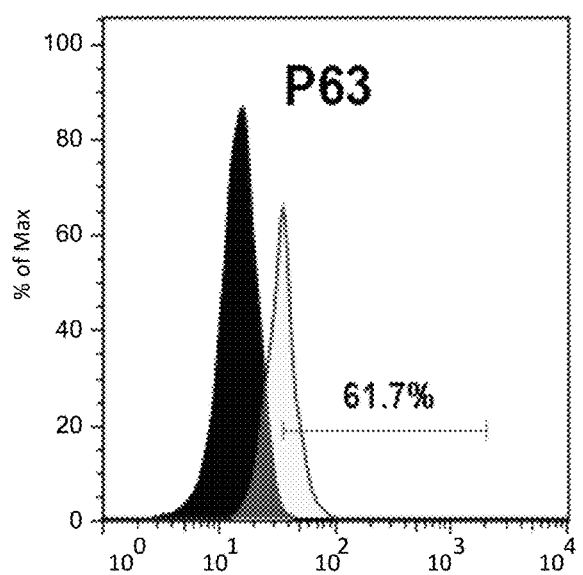
FIG. 12H

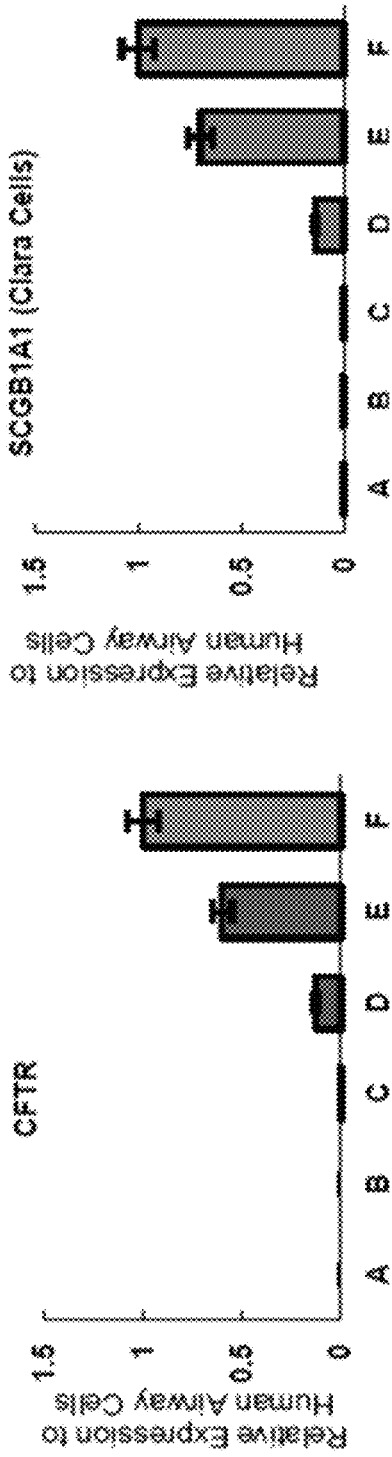
FIG. 13A
FIG. 13B
FIG. 13C
FIG. 13D

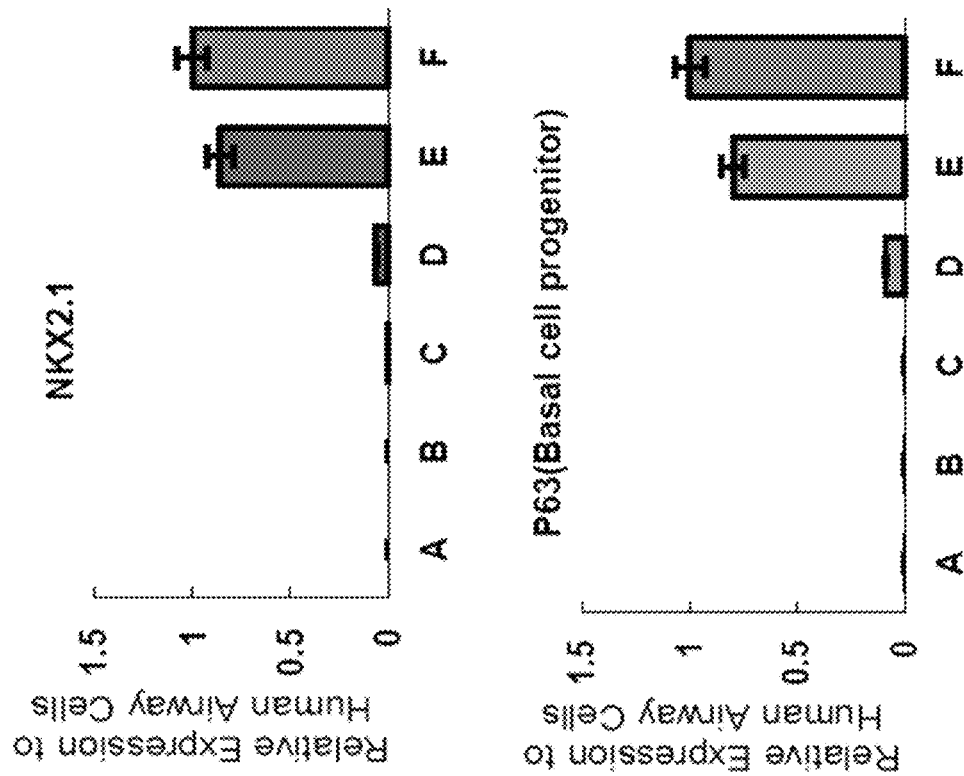
FIG. 17C  FIG. 17D  FIG. 17A  FIG. 17B
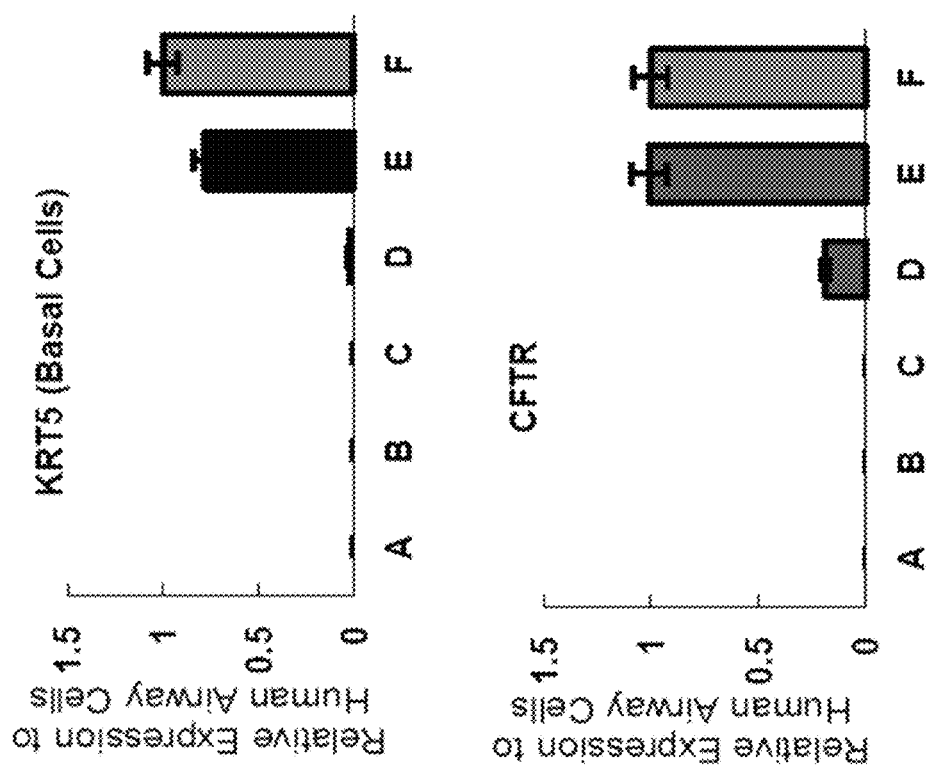

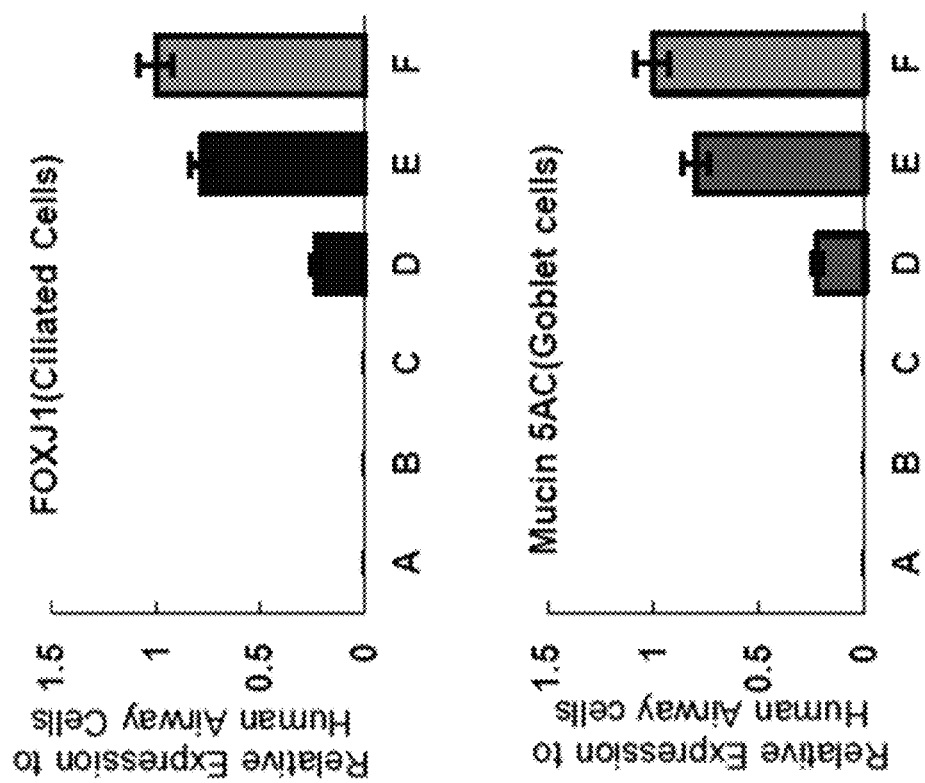
FIG. 17F
FIG. 17G
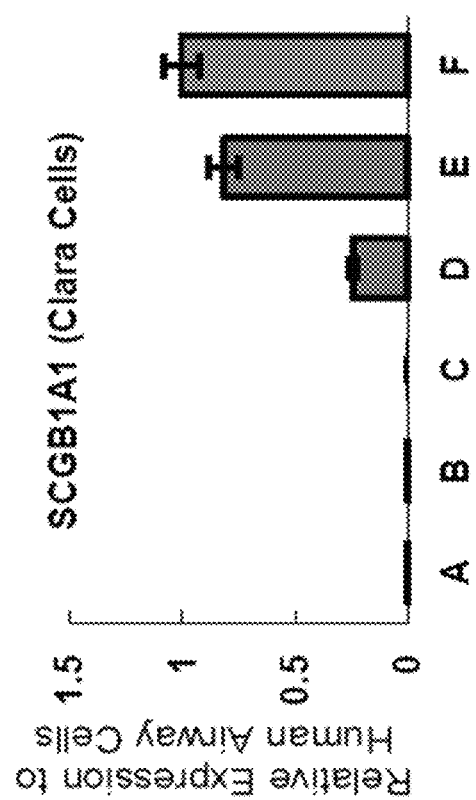
FIG. 17E

FIG. 19A 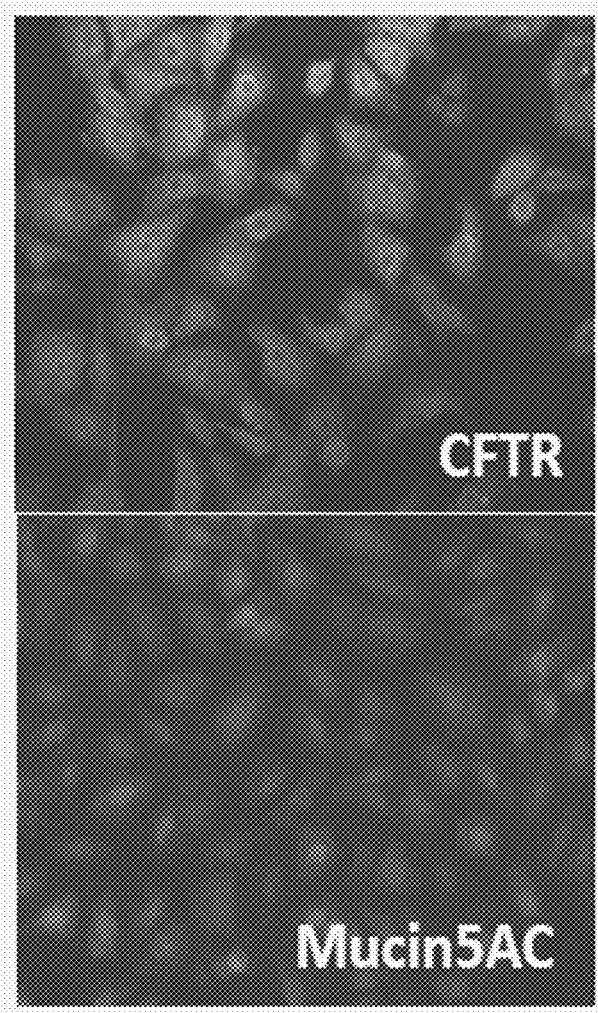 FIG. 19B
FIG. 19C 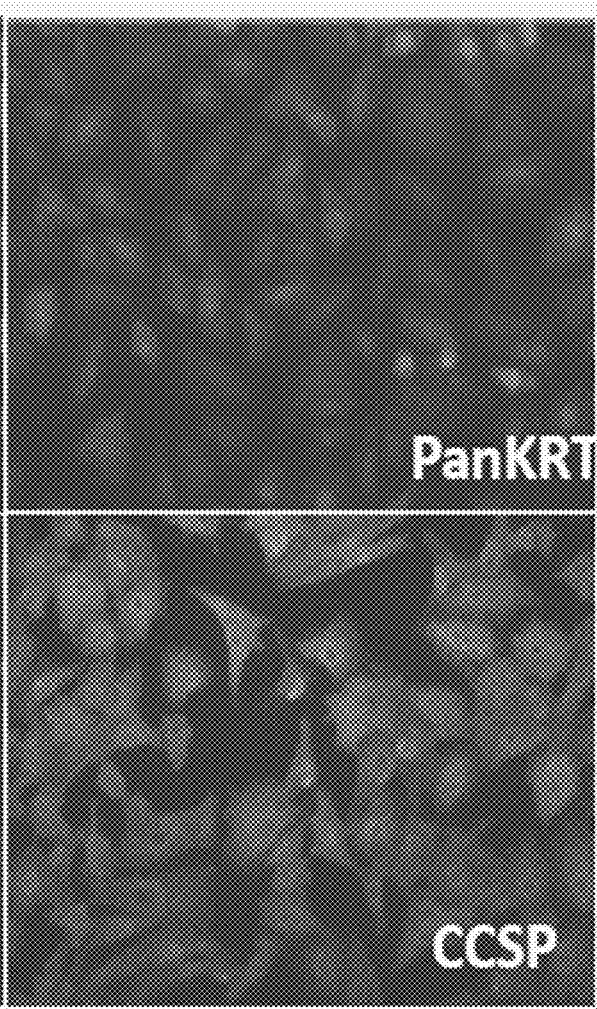 FIG. 19D

FIG. 20A
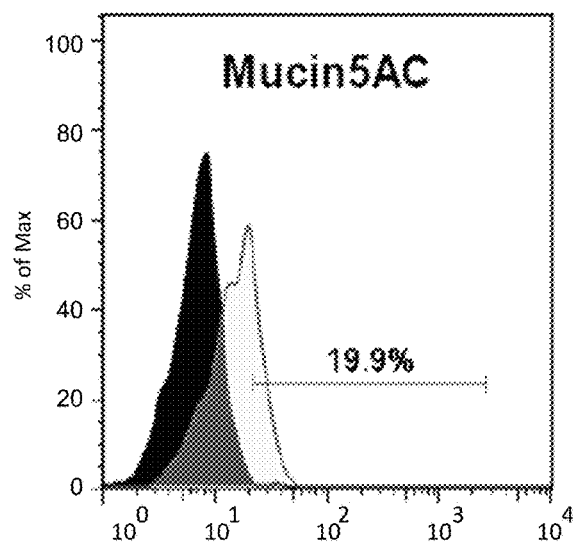
FIG. 20B
FIG. 20C
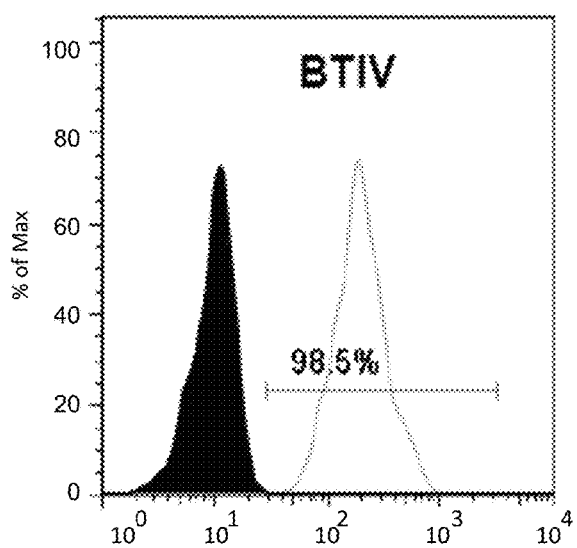
FIG. 20D

FIG. 20E
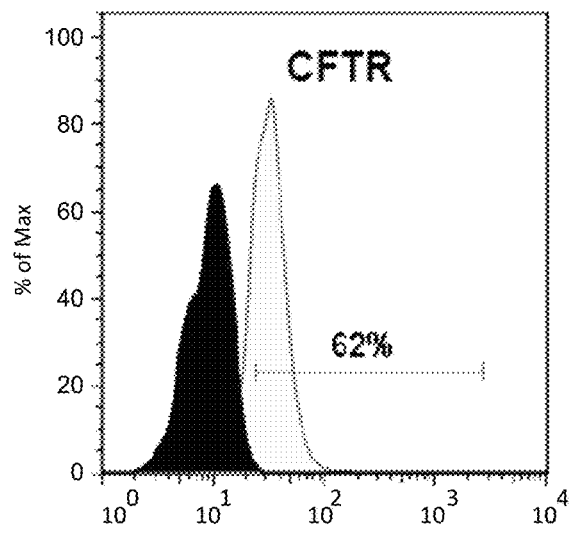
FIG. 20F
FIG. 20G
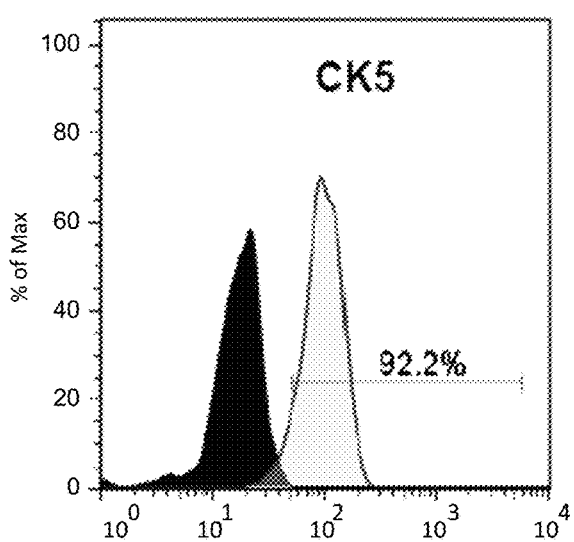
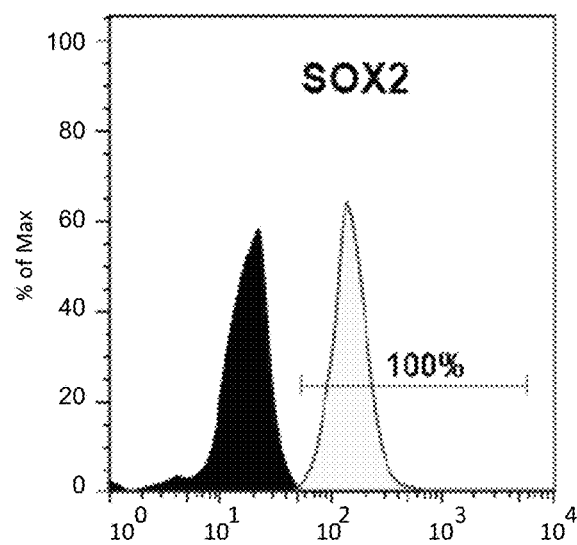
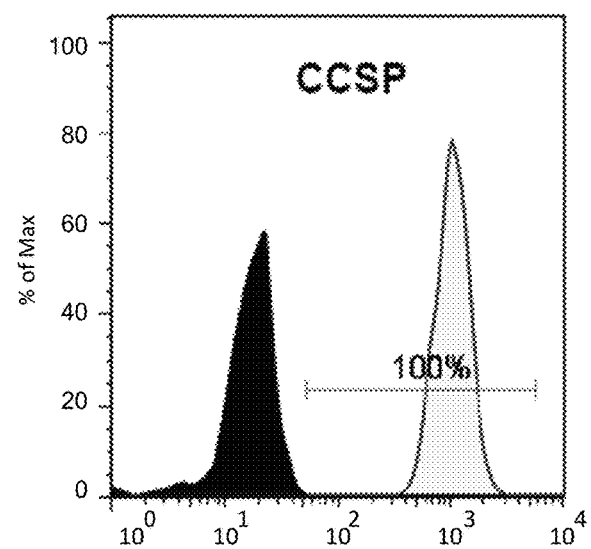
FIG. 20H

FIG. 22A
P63 expression in Lung Organoid in Matrigel
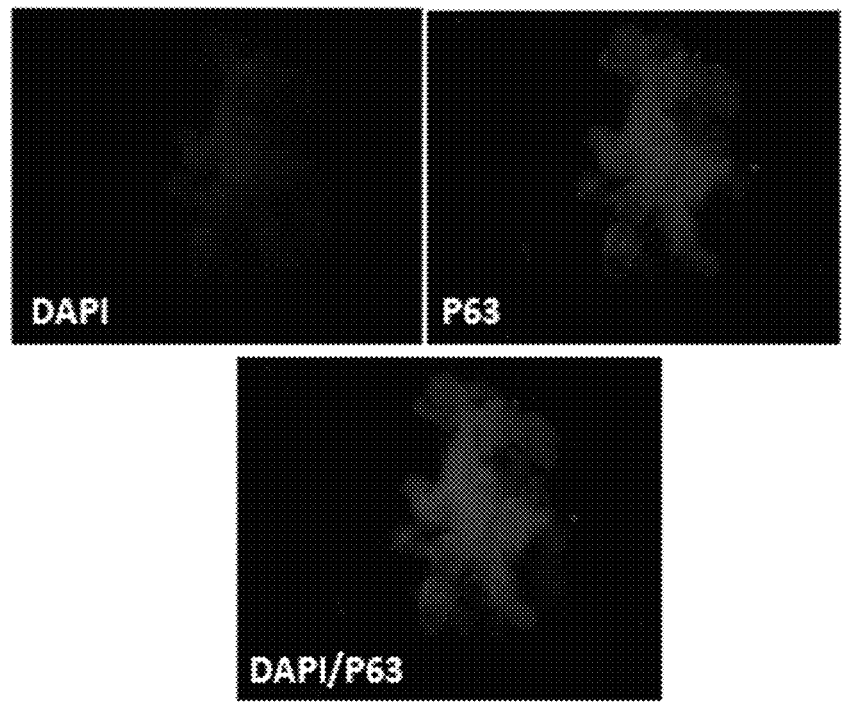
NKX2.1 expression in Lung Organoid in Matrigel
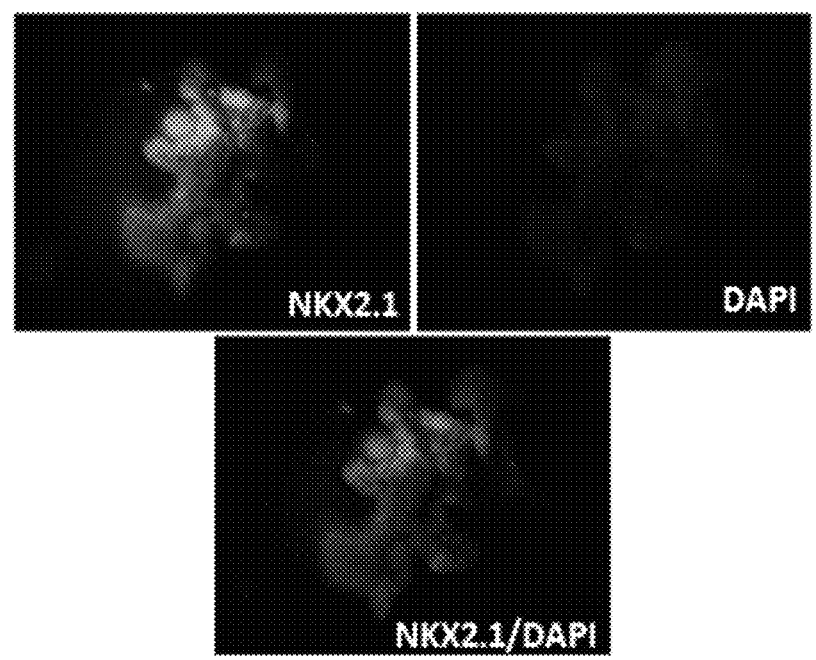
FIG. 22B

COMPOSITIONS AND METHODS OF PREPARING AIRWAY CELLS

CROSS-REFERENCE TO RELATED APPLICATIONS

The present application is a 35 U.S.C. § 371 national phase application from, and claims priority to, International Application No. PCT/US2015/011284, filed Jan. 14, 2015, and published under PCT Article 21(2) in English, which claims priority under 35 U.S.C. § 119(e) to U.S. Provisional Application No. 61/927,097, filed Jan. 14, 2014, the entire disclosure of which is incorporated by reference herein as if set forth herein in its entirety.

STATEMENT REGARDING FEDERALLY SPONSORED RESEARCH OR DEVELOPMENT

This invention was made with government support under HL111016 awarded by National Institutes of Health. The government has certain rights in the invention.

BACKGROUND OF THE INVENTION

Approximately 30,000 people in the United States have cystic fibrosis (CF) and about 1,000 new cases of CF are diagnosed each year. CF is an autosomal recessive genetic disorder that affects most critically the lungs, and also the pancreas, liver, and intestine. It is characterized by abnormal transport of chloride and sodium across the epithelium, leading to thick, viscous secretions. The most common cause of death in people with CF is respiratory failure. Several studies have shown that mutations in the cystic fibrosis transmembrane conductance regulator (CFTR) gene can impair folding, secretion, cell surface stability, and/or function of the CFTR chloride channel across an epithelium. Although an intense effort is underway to identify compounds that target the CFTR structural defect, so far their clinical efficacy has proven to be poor, highlighting the necessity to better understand the molecular mechanism of CFTR regulation that is a prerequisite for developing more efficient therapies.

In the airways, the CFTR mutations have a large impact on proximal airway epithelial cells. One of the major roadblocks in CF research is the lack of live human proximal airway epithelial cells, the cell type selectively impacted by CFTR mutations, for use in mechanistic studies and drug discovery. Animal models of CF generally do not recapitulate the human condition very well.

Induced pluripotent stem (iPS) cells have been shown to display the potential to develop into alveolar epithelial cells. Several research groups have reported the differentiation of ESCs and iPS cells toward alveolar type II cells, using a variety of protocols. However, many aspects of these profoundly important airway diseases remain poorly understood.

Therefore, a need exists in the art for identifying a reliable source of functional airway epithelial cells to be used in lung-related therapies.

SUMMARY OF THE INVENTION

The invention includes compositions and methods of preparing airway epithelial cells that may be used in tissue engineering and for treating respiratory disorders.

In one aspect, the invention includes an airway epithelial cell derived from an induced pluripotent stem (iPS) cell characterized by expression of airway cell surface markers, wherein the airway cell surface markers comprise Clara cell secretory protein (CCSP), cytokeratin 5 (KRT5), and FOXJ1, and an ability to proliferate in culture without loss of the airway cell surface markers. In one aspect, the invention includes a method of differentiating an induced pluripotent stem (iPS) cell into an airway epithelial cell comprising culturing the iPS cell in the absence of serum to induce differentiation into a definitive endoderm (DE) cell, culturing the DE cell in the presence of serum to induce differentiation into an anterior foregut endoderm (AFE) cell, and culturing the AFE cell in the presence of serum, a cytokine cocktail, and a high concentration of retinoic acid to induce differentiation of the AFE cell into the airway epithelial cell. In another aspect, the invention includes a method of engineering a three-dimensional lung tissue comprising differentiating a population of induced pluripotent stem (iPS) into airway epithelial cells, wherein the airway epithelial cells express airway cell surface markers comprising Clara cell secretory protein (CCSP), cytokeratin 5 (KRT5), and FOXJ1; and are capable of proliferation in culture without loss of the airway cell markers, and seeding the airway epithelial cells onto a three-dimensional scaffold. In yet another aspect, the invention includes an engineered three-dimensional lung tissue comprising the airway epithelial cell described herein.

In various embodiments of the above aspects or any other aspect of the invention delineated herein, the invention includes the airway epithelial cell that is ciliated. In another embodiment, the airway epithelial cell is derived from a cystic fibrosis human iPS cell. In yet another embodiment, the airway epithelial cell is capable of proliferation in culture for at least about 30 days, such as greater than about 30 days.

In another embodiment, the expression of airway cell surface markers further comprises cystic fibrosis transmembrane conductance regulator protein (CFTR), and/or at least one of β-tubulin IV, mucin-5AC, and P63. In yet another embodiment, the airway cell surface markers are expressed at levels comparable to those expressed on freshly isolated human airway cells.

In one embodiment, the culturing the iPS cell comprises culturing the iPS cell in the presence of activin A. In such embodiment, the activin A is at about saturating concentrations in the iPS cell culture. In another embodiment, culturing the iPS cell comprises culturing the iPS cells in the presence of a serum-free supplement.

In one embodiment, DE cell expresses one or more definitive endoderm cell markers selected from the group consisting of c-kit, SOX17, FOXA2, and CXCR4. In such embodiments, culturing in the presence of ECM molecules comprises dissociating the DE cell prior to culturing with ECM molecules. Also, the ECM molecules may comprise one or more of a collagen, laminin, fibronectin, tenascin, elastin, a proteoglycan, and a glycosaminoglycan. In another embodiment, culturing the DE cell comprises sequentially exposing the DE cell to small molecular inhibitors to suppress posterior endoderm fate and induce proximal endoderm fate, such as small molecular inhibitors that inhibit BMP/TGF signaling like dorsomorphin, Noggin, A83-01, DMH-1, D4476, GW788388, LY364947, RepSox, SB431542, SB505124, SB525334, and SD208. Also, the small molecular inhibitors may inhibit TGF/WNT signaling, such as IWR-1, Noggin, CCT036477, IWP2, demethoxy curcumin, FH535 A83-01, D4476, GW788388, LY364947, RepSox, SB431542, SB505124, SB525334, and SD208.

In another embodiment, the AFE cell expresses NKX2.1.

In yet another embodiment, the high concentration of retinoic acid comprises at least about 0.5 µM of retinoic acid, such as about 1 µM.

In another embodiment, the cytokine cocktail inhibits the WNT pathway.

In still another embodiment, the iPS cell is derived from a diseased human cell, such as a cystic fibrosis disease-specific human iPS cell.

In another aspect, the invention includes a method of improving, treating or relieving a symptom of a respiratory disorder in a subject in need thereof comprising differentiating an induced pluripotent stem (iPS) into an airway epithelial cell, wherein the airway epithelial cells express airway cell surface markers comprising Clara cell secretory protein (CCSP), cytokeratin 5 (KRT5), and FOXJ1, and are capable of proliferation in culture without loss of the airway cell markers, and administering the airway epithelial cells in an amount effective to treat the respiratory disorder in the subject.

In various embodiments of the above aspects or any other aspect of the invention delineated herein, the invention includes airway epithelial cells that form an organoid structure.

In another embodiment, the three-dimensional scaffold comprises matrigel.

BRIEF DESCRIPTION OF THE DRAWINGS

FIG. 6A shows the ex vivo differentiated NKX2.1$^+$ cells stained with DAPI.

FIG. 6B shows the ex vivo differentiated NKX2.1$^+$ cells stained with FOXA2.

FIG. 6C shows the ex vivo differentiated NKX2.1$^+$ cells stained with NKX2.1.

FIG. 6D shows the ex vivo differentiated NKX2.1$^+$ cells co-stained with NKX2.1/FOXA2/DAPI, suggesting that the NKX2.1$^+$ cells were differentiated in vitro.

FIG. 7A shows the ex vivo differentiated NKX2.1$^+$/SOX2$^+$ stained with DAPI.

FIG. 7B shows the ex vivo differentiated NKX2.1$^+$/SOX2$^+$ stained with SOX2.

FIG. 7C shows the ex vivo differentiated NKX2.1$^+$/SOX2$^+$ stained with NKX2.1.

FIG. 7D shows the ex vivo differentiated NKX2.1$^+$/SOX2$^+$ stained with SOX2/NKX2.1/DAPI, suggesting that the NKX2.1$^+$/SOX2$^+$ cells were differentiated in vitro.

FIG. 10B shows quantitative RT-PCR of KRT5 at day 20 results in mature lung airway epithelial cells.

FIG. 10C shows quantitative RT-PCR of CFTR at day 20 results in mature lung airway epithelial cells.

FIG. 10D shows quantitative RT-PCR of CCSP or SCGB1A1 at day 20 results in mature lung airway epithelial cells.

FIG. 10E shows quantitative RT-PCR of P63 at day 20 results in mature lung airway epithelial cells.

FIG. 12E shows flow cytometric analysis of the cell population derived from iPS cells at day 27 expressing CCSP.

FIG. 12F shows flow cytometric analysis of the cell population derived from iPS cells at day 27 expressing KRT5.

FIG. 12G shows flow cytometric analysis of the cell population derived from iPS cells at day 27 expressing Mucin5AC.

FIG. 12H shows flow cytometric analysis of the cell population derived from iPS cells at day 27 expressing P63.

FIG. 13A shows quantitative RT-PCR of CFTR at day 27 at day 27 results in mature lung airway epithelial cells.

FIG. 13B shows quantitative RT-PCR of FOXJ1 at day 27 at day 27 results in mature lung airway epithelial cells.

FIG. 13C shows quantitative RT-PCR of SCGB1A1 (CCSP) at day 27 results in mature lung airway epithelial cells.

FIG. 13D shows quantitative RT-PCR of Mucin5AC at day 27 results in mature lung airway epithelial cells.

FIG. 17A shows quantitative RT-PCR of KRT5 or CK5 at day 35 results in iPS derived airway epithelial cells.

FIG. 17B shows quantitative RT-PCR of CFTR at day 35 results in iPS derived airway epithelial cells.

FIG. 17C shows quantitative RT-PCR of NKX2.1 at day 35 results in iPS derived airway epithelial cells.

FIG. 17D shows quantitative RT-PCR of P63 at day 35 results in iPS derived airway epithelial cells.

FIG. 17E shows quantitative RT-PCR of SCGB1A1 or CCSP at day 35 results in iPS derived airway epithelial cells.

FIG. 17F shows quantitative RT-PCR of FOXJ1 at day 35 results in iPS derived airway epithelial cells.

FIG. 17G shows quantitative RT-PCR of Mucin5AC at day 35 results in iPS derived airway epithelial cells.

FIG. 19A shows airway epithelial cells derived from CF disease-specific human iPS cells stained with CFTR antibody.

FIG. 19B shows airway epithelial cells derived from CF disease-specific human iPS cells stained with Mucin5AC antibody.

FIG. 19C shows airway epithelial cells derived from CF disease-specific human iPS cells stained with PanKRT antibody.

FIG. 19D shows airway epithelial cells derived from CF disease-specific human iPS cells stained with CCSP antibody.

FIG. 20A shows flow cytometric analysis of Mucin5AC in airway epithelial cells derived from CF disease-specific human iPS cells.

FIG. 20B shows flow cytometric analysis of P63 in airway epithelial cells derived from CF disease-specific human iPS cells.

FIG. 20C shows flow cytometric analysis of β-tubulin IV in airway epithelial cells derived from CF disease-specific human iPS cells.

FIG. 20D shows flow cytometric analysis of FOXJ1 in airway epithelial cells derived from CF disease-specific human iPS cells.

FIG. 20E shows flow cytometric analysis of CFTR in airway epithelial cells derived from CF disease-specific human iPS cells.

FIG. 20F shows flow cytometric analysis of SOX2 in airway epithelial cells derived from CF disease-specific human iPS cells.

FIG. 20G shows flow cytometric analysis of CK5 or KRT5 in airway epithelial cells derived from CF disease-specific human iPS cells.

FIG. 20H shows flow cytometric analysis of CCSP in airway epithelial cells derived from CF disease-specific human iPS cells.

FIG. 22A is a panel of images showing positive P63 immunostaining of airway progenitor cells derived from iPSCs that developed into lung organoid structures in Matrigel.

FIG. 22B is a panel of images showing positive NKX2.1 immunostaining of airway progenitor cells derived from iPSCs that developed into lung organoid structures in Matrigel.

DETAILED DESCRIPTION OF THE INVENTION

Definitions

Figure 1:
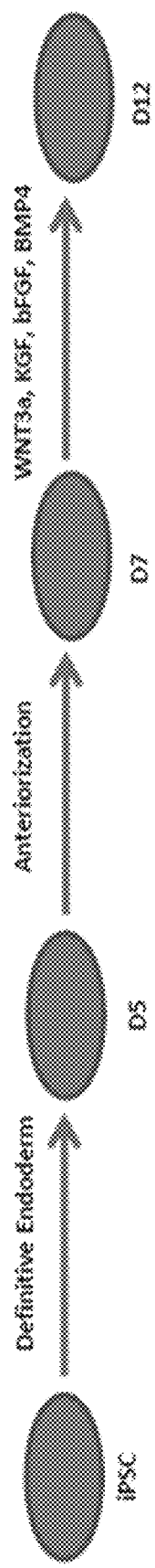
FIG. 1 diagrams the steps of differentiating human iPS cells into airway epithelial cells.

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

By "anterior foregut endoderm" is endoderm that is anterior to the endoderm that gives rise to the liver. One of ordinary skill in the art will readily appreciate that "anterior foregut endoderm" thus includes, for example, pharyngeal endoderm and other, more highly differentiated populations of endodermal cells and that the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx.

The term "differentiation" as used herein refers to the process by which a less specialized cell, such as a stem cell or induced pluripotent stem cell, becomes a more specialized cell type, such that it is committed to a specific lineage including, without limitation, certain progenitor cells as well as more specialized somatic cells. Conditions for differentiation of stem cells are well known in the art.

"Differentiation medium" as used herein to refers to a cell growth medium comprising an additive or a lack of an additive such that a stem cell, induced pluripotent cell or other such progenitor cell that is not fully differentiated, develops into a cell with some or all of the characteristics of a differentiated cell or cell that is more differentiated than the stem cell, induced pluripotent cell or other such progenitor cell when incubated in the medium.

By "definitive endoderm cell" is meant a cell expressing one or more markers of the definitive endoderm lineage. These markers can include, but are not limited to, CXCR4, SOX17, GATA-4, FOXA2, AFP, CER1, C-KIT, EPCAM, SNAI1, GSC, E-Cad, or N-Cad. Definitive endoderm is defined functionally by cells that are capable of further differentiating towards one or more of the tissues that are derived from the endoderm germ layer. This can include the lungs, thyroid, liver, pancreas, or intestines.

By "airway epithelial cell" is meant an epithelial cell that makes up a layer of cells that line the large airways (bronchi) and small airways (bronchioles). Airway epithelial cells include ciliated, secretory, basal and columnar cell types.

By "induced pluripotent stem cell" or "iPS cell" is meant a type of pluripotent stem cell artificially derived (using genetical or chemical methods) from a non-pluripotent cell—typically an adult somatic cell—by inducing expression of specific genes. The induced pluripotent stem cell is substantially similar to natural pluripotent stem cells. The induced pluripotent stem cell is capable of differentiating into multiple cell types including, but not limited to, definitive endoderm cells, anterior foregut endoderm cells, and airway epithelial cells.

The term "organoid" refers to a three-dimensional aggregation of one or more cell types that mimics the superficial appearance or actual structure or function of a tissue or organ.

The terms "induction" or "induce", as relating to the process or act of causing to occur a specific effect on the phenotype of cell. Such effect can be in the form of causing a change in the phenotype, e.g., differentiation to another cell phenotype, or can be in the form of maintaining the cell in a particular cell, e.g., preventing dedifferentiation or promoting survival of a cell.

The term "pluripotent" as used herein refers to an undifferentiated cell that maintains the ability to allow differentiation into various cell types.

The terms "precursor cell," "progenitor cell," and "stem cell" are used interchangeably in the art and as used herein refer either to a pluripotent or lineage-uncommitted progenitor cell, which is potentially capable of an unlimited number of mitotic divisions to either renew itself or to produce progeny cells which will differentiate into the desired cell type. In contrast to pluripotent stem cells, lineage-committed progenitor cells are generally considered to be incapable of giving rise to numerous cell types that phenotypically differ from each other. Instead, progenitor cells give rise to one or possibly two lineage-committed cell types. In one embodiment, the stem cell is an induced pluripotent stem (iPS) cell.

By "respiratory disorder" is meant a disease or condition that is physically manifested in the respiratory tract including, but not limited to, cystic fibrosis, respiratory distress syndrome, acute respiratory distress syndrome, pulmonary tuberculosis, cough, bronchial asthma, cough based on increased airway hyperreactivity (bronchitis, flu syndrome, asthma, obstructive pulmonary disease, and the like), flu syndrome, anti-cough, airway hyperreactivity, tuberculosis disease, asthma (airway inflammatory cell infiltration, increased airway hyperresponsiveness, bronchoconstriction, mucus hypersecretion, and the like), chronic obstructive pulmonary disease, emphysema, pulmonary fibrosis, idiopathic pulmonary fibrosis, cough, reversible airway obstruction, adult respiratory disease syndrome, pigeon fancier's disease, farmer's lung, bronchopulmonary dysplasia, airway disorder, emphysema, allergic bronchopulmonary aspergillosis, allergic bronchitis bronchiectasis, occupational asthma, reactive airway disease syndrome, intersitial lung disease, parasitic lung disease, and the like.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By "effective amount" is meant the amount required to reduce or improve at least one symptom or change in a clinical marker of a respiratory disorder, condition or disease relative to an untreated patient. The effective amount of airway epithelial cells used for therapeutic treatment of the respiratory disorder, condition or disease varies depending upon the manner of the specific disorder, condition or disease, extent of the disorder, condition or disease, and administration of the cells, as well as the age, body weight, and general health of the subject.

"Expandability" is used herein to refer to the capacity of a cell to proliferate, for example, to expand in number or, in the case of a population of cells, to undergo population doublings.

The term "expression" as used herein is defined as the transcription and/or translation of a particular nucleotide sequence driven by its promoter.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a cell is purified if it is substantially free of cells or materials. Purity and homogeneity are typically determined using analytical techniques, for example, flow cytometry or flow activated cell sorting. The term "purified" can denote that a cell gives rise to essentially one population.

As used herein, "phenotype" refers to the entire physical, biochemical, and physiological makeup of a cell, e.g., having any one trait or any group of traits.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," treating," "treatment," and the like refer to reducing or improving a respiratory disorder, condition or disease and/or one or more symptoms associated therewith. It will be appreciated that, although not precluded, treating a respiratory disorder, condition or disease does not require that the disorder, condition, disease or symptoms associated therewith be completely ameliorated or eliminated.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Airway Epithelial Cells

The development of alternative sources of donor lung would change the paradigm of treatment of diseases of the lung. One option to treat end stage lung disease is transplantation with engineered lungs made from patient-specific cells. The discovery of iPS cell-derived airway epithelial cells not only facilitates the study of basic lung pathology, but also facilitates the development of novel therapies for treatment of lung disease, including CF. The airway epithelial cells derived from an iPS cell as described herein offer a unique opportunity for a cell-based therapeutic application and potential replacement of diseased lung epithelia.

In one aspect, an airway epithelial cell derived from an induced pluripotent stem (iPS) cell is included in the present invention. The airway epithelial cell is characterized by expression of airway cell surface markers, such as Clara cell secretory protein (CCSP), cytokeratin 5 (KRT5), and FOXJ1. The airway epithelial cell also has an ability to proliferate in culture without loss of the airway cell surface markers. Airway epithelial cells include ciliated, secretory, basal and columnar cell types. In one embodiment, the airway epithelial cell is ciliated.

Airway epithelial cell derived from an iPS cell also express an array of airway specific cell surface markers. Examples of airway cell surface markers include, but are not limited to, Mucin1 or MUC1, Mucin5AC, FOXJ1, CCSP, KRT5, KRT14, TRP63, SOX17, SOX2, β-Tubulin IV and CFTR.

Mucin1 or MUC1 is a member of the mucin family and is a membrane bound, glycosylated phosphoprotein. The protein is anchored to the apical surface of many epithelia by a transmembrane domain. Exemplary Mucin1 sequences include human MUC1 sequence found at GenBank Accession No. NM_001018016 or NP_001018016, or a fragment thereof, and the mouse Muc1 sequence found at NM_013605 or NP_038633, or a fragment thereof.

Mucin5AC is a glycoprotein found in gastric and respiratoy tract epithelia. An exemplary Mucin5AC sequence includes human MUC5AC sequence found at GenBank Accession No. XM_003403450 or P98088, or a fragment thereof.

Forkhead box J1 (FOXJ1) is a transcription factor involved in ciliogenesis. Exemplary FOXJ1 sequences include human FOXJ1 sequence found at GenBank Accession No. NM_001454 or NP_001445, or a fragment thereof, and the mouse FoxJ1 sequence found at NM_008240 or NP_032266, or a fragment thereof.

Clara cell secretory protein (CCSP) is an immune-modulating and anti-inflammatory agent. Exemplary CCSP sequences include human CCSP sequence found at GenBank Accession No. NM_003357 or NP_003348, or a fragment thereof, and the mouse CCSP sequence found at NM_011681 or NP_035811, or a fragment thereof.

Keratin 5 (KRT5) belongs to a group of tough, fibrous proteins that form the structural framework of keratinocytes. Exemplary KRT5 sequences include human KRT5 sequence found at GenBank Accession No. NM_000424 or NP_000415, or a fragment thereof, and the mouse KRT5 sequence found at NM_027011 or NP_081287, or a fragment thereof.

Keratin 14 (KRT14) is a member of the type I keratin family of intermediate filament proteins. Exemplary KRT14 sequences include human KRT14 sequence found at GenBank Accession No. NM_000526 or NP_000517, or a fragment thereof, and the mouse KRT14 sequence found at NM_016958 or NP_058654, or a fragment thereof.

Transformation related protein 63 (TRP63 or P63) is a member of the p53 family of transcription factors involved in cellular responses to stress and development. Exemplary TRP63 sequences include human TRP63 sequence found at GenBank Accession No. NM_001114978 or NP_001108450, or a fragment thereof, and the mouse TRP63 sequence found at NM_001127259 or NP_001120731, or a fragment thereof.

Sex determining region Y-box 17 (SOX17) is a transcription regulator that binds target promoter DNA and plays a key role in the regulation of embryonic development. An exemplary SOX17 sequence includes the human SOX17 sequence found at GenBank Accession No. NM_022454 or NP_071899, or a fragment thereof.

Sex determining region Y-box 2 (SOX2) is a transcription factor that is essential for maintaining self-renewal, or pluripotency, of undifferentiated embryonic stem cells. Exemplary CFTR sequences include the human CFTR sequence found at GenBank Accession No. NM_003106 or NP_003097, or a fragment thereof, and the mouse CFTR sequence found at NM_011443 or NP_035573, or a fragment thereof.

β-Tubulin IV is one of several members of a small family of globular proteins. β-Tubulin IV is present in ciliated cell types and may be required for axonemal structures in mammals.

As described elsewhere herein, CFTR is a protein involved in the transport of chloride ions across cell membranes. Exemplary CFTR sequences include human CFTR sequence found at GenBank Accession No. NM_000492 or NP_000483, or a fragment thereof, and the mouse CFTR sequence found at NM_021050 or NP_066388, or a fragment thereof.

In one embodiment, the airway epithelial cell derived from an iPS cell includes the expression of airway cell surface marker CFTR. In another embodiment, the airway cell surface markers include β-tubulin IV, mucin-5AC, and P63. The expressions of the airway cell surface markers in the airway epithelial cell are comparable to levels expressed on freshly isolated human airway cells.

Unlike isolated airway cells, airway epithelial cells derived from an iPS cell are capable of proliferating for several passages without losing airway epithelial cell-associated markers, such as CCSP, P63, FOXJ1, CFTR and MUC5AC. The proliferation capacity of the cells can be used to generate millions of cells for different purposes. The ability to "scale up" a progenitor population isparticularly valuable when translating these technologies for use in producing tissue engineered human lung tissues, using autologous iPS cell derived cells. In one embodiment, the airway epithelial cell is capable of proliferation in culture for at least about 30 days. In another embodiment, the airway epithelial cell is capable of proliferation in culture for greater than about 30 days.

Differentiation into Airway Epithelial Cells

The invention further provides, in one aspect, methods of differentiating an induced pluripotent stem (iPS) cell into an airway epithelial cell. The methods include culturing the iPS cell in the absence of serum to induce differentiation into a definitive endoderm (DE) cell, culturing the DE cell in the presence of serum to induce differentiation into an anterior foregut endoderm (AFE) cell, and culturing the AFE cell in the presence of serum in a cytokine cocktail and a high concentration of retinoic acid to induce differentiation of the AFE cell into the airway epithelial cell.

iPS Cells

The iPS cells that can be used with the invention can be derived using approaches substantially similar to the originally described approach from 2006 (Yamanaka et al., Cell Stem Cell 1:39-49 (2007)) or modifications that are known to those of skill in the art. For example, iPS cells can be created by modifying the insertion method of genes into the host cellular DNA. See, for example, Wernig et al., PNAS, 105:5856-5861 (2008); Jaenisch et al., Cell 132:567-582 (2008); Hanna et al., Cell 133:250-264 (2008); and Brambrink et al., Cell Stem Cell 2:151-159 (2008). These references are incorporated by reference in their entireties for teaching iPS cells and methods for producing them.

Since iPS cells are derived from somatic cells that have been reprogrammed into pluripotent stem cells, multiple cell types can be used to generate the iPS cells. For example, treatments with autologous cells from a subject with a respiratory disorder, such as cystic fibrosis, will moderate or prevent immunological rejection of the cells. Therefore, it is useful to generate iPS cells from a subject that will receive treatment with differentiated cells derived from their iPS cells. In one embodiment, the airway epithelial cell is derived from a diseased cell, such as a cystic fibrosis human iPS cell. In another embodiment, the airway epithelial cell is derived from a cell that is autologous to a subject with a respiratory disorder.

The method of differentiating the iPS cell into the airway epithelial cell includes culturing the iPS cells to induce differentiation into DE cells. In one embodiment, the iPS cells are cultured in the absence of serum. In another embodiment, the iPS cells are cultured in the presence of a serum-free supplement. Examples of serum-free supplements can include, but are not limited to, serum replacement (Sigma, St. Louis, Mo.), B-27 (Life Technologies, Carlsbad, Calif.), BIOGRO-2 (BI, Israel), KnockOut™ (Life Technologies, Carlsbad, Calif.), PluriQ (GlobalStem, Rockville, Md.), TCH® (MP, Santa Ana, Calif.), and other similar supplements.

In one embodiment, the iPS cells may be cultured in the presence of an agent, molecule or compound that induces differentiation to definitive endoderm cells, including but not limited to activin A, nodal protein, an agonist of activin A, an antagonist of inhibin, or any combination thereof. For example, the cells may be cultured with an agent, molecule or compound that activates an activin A receptor, such as activin A or an activin A receptor agonist. In another example, the cells may be cultured with an agent, molecule or compound that provides an activation signal or stimulates the cells in a manner similar to activin A, such as nodal protein, resulting in differentiation of the iPS cells into definitive endoderm cells. In yet another example, the cells may be cultured with an agent, molecule or compound, such as an antagonist of an activin A inhibitor, e.g., an inhibitor of inhibin, or other antagonistic molecule that may indirectly activate the activin A receptor or induce differentiation to a definitive endoderm cell.

The concentration of one or more agents, molecules or compounds, such as activin A, that induce differentiation of iPS cells to definitive endoderm cells can be in the range of about 5 ng/ml to about 500 ng/ml. The concentration of one or more agents, molecules or compounds, such as activin A, can be about 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 ng/ml, 175 ng/ml, 200 ng/ml, 225 ng/ml, 250 ng/ml, 275 ng/ml, 300 ng/ml, 350 ng/ml, 400 ng/ml, 450 ng/ml, 550 ng/ml, or any concentraion in between. In one embodiment, the iPS cell is cultured in the presence of 100 ng/ml of one or more agents, molecules or compounds, such as activin A, to induce differentiation of iPS cells to definitive endoderm cells. The concentration of the agent, molecule or compound, such as activin A, to induce differentiation to definitive endoderm cells can also be at about saturating concentrations in the iPS cell culture. Saturating concentrations of activin A is about 5 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 ng/ml, 175 ng/ml, 200 ng/ml, 225 ng/ml, 250 ng/ml, 275 ng/ml, 300 ng/ml, 350 ng/ml, 400 ng/ml, 450 ng/ml, 550 ng/ml, or more. In another embodiment, the concentration of the agent, molecule, or compound, such as activin A, to induce differentiation to definitive endoderm cells is at about saturating concentrations in the iPS cell culture.

The iPS cells can be cultured for at least about 12 hrs, 16 hrs, 20 hrs, 24 hrs, 30 hrs, 36 hrs, 48 hrs, 3 days, 4 days, 5 days, 6 days, 7 days, 8 days, 9 days, or more. In one embodiment, the iPS cells are cultured for about 5 days. In one embodiment, the iPS cells are cultured for about 5 days. The iPS cells can be cultured in the presence of activin A for at least about 6 hours. The iPS cells can be cultured for at least about 12 hrs, 16 hrs, 20 hrs, 24 hrs, 30 hrs, 36 hrs, 48 hrs, 3 days, 4 days, 5 days, 6 days, 7 days, 8 days, 9 days, or more. In another embodiment, the iPS cells are cultured in the presence of activin A for at least about 5 days.

Differentiation of iPS cells can occur using the embroid body method or directly on feeder layers or Matrigel to the definitive endoderm stage.

Definitive Endoderm Cells

The DE cells differentiated from the iPS cells express an array of definitive endoderm cell markers. Examples of definitive endoderm cell markers include, but are not limited to, c-kit, SOX17, FOXA2, and CXCR4.

CD117 or c-kit is a protein that in humans is encoded by the KIT gene. Exemplary c-kit sequences include human c-kit sequence found at GenBank Accession No. NM_000222 or NP_000213, or a fragment thereof, and the mouse c-kit sequence found at NM_001122733 or NP_001116205, or a fragment thereof.

CXCR4 is an alpha-chemokine receptor specific for stromal-derived-factor-1. Exemplary CXCR4 sequences include human CXCR4 sequence found at GenBank Accession No. NM_001008540 or NM_001008540, or a fragment thereof, and the mouse CXCR4 sequence found at NM_009911 or NP_034041, or a fragment thereof.

In one embodiment, the DE cell differentiated from an iPS cell includes the expression of endoderm cell surface markers, c-kit, SOX17, FOXA2, and CXCR4.

The method of differentiating the iPS cell into the airway epithelial cell also includes culturing the DE cell in the presence of serum to induce differentiation into an anterior foregut endoderm (AFE) cell. In one embodiment, the DE cells are cultured in the presence of serum. In another embodiment, the DE cells are cultured in the presence of extracellular matrix (ECM) molecules. Examples of ECM molecules can include, but are not limited to, collagens, laminins, fibronectins, tenascins, elastins, proteoglycans, glycosaminoglycans, polysaccharides, celluloses, other molecules found in the ECM, and any combinations thereof.

The DE cells can be dissociated prior to culturing in the presence of ECM molecules. The media can also be changed from DE cell induction media to AFE cell induction media. In one embodiment, the iPS cells are cultured in the presence of serum.

The DE cells are sequentially exposed to small molecule inhibitors to suppress posterior endoderm fate and induce proximal endoderm fate. The DE cells can also be cultured in the presence of ECM molecules while sequentially exposing the DE cells to small molecule inhibitors that inhibit BMP/TGF signaling and small molecular inhibitors that inhibit TGF/WNT signaling. The small molecule inhibitors that inhibit BMP/TGF signaling can include, but are not limited to, dorsomorphin, Noggin, A83-01, DMH-1, D4476, GW788388, LY364947, RepSox, SB431542, SB505124, SB525334, SD208, and any combinations thereof. The small molecule inhibitors that inhibit TGF/WNT signaling can include, but are not limited to, IWR-1, Noggin, CCT036477, IWP2, demethoxy curcumin, FH535 A83-01, D4476, GW788388, LY364947, RepSox, SB431542, SB505124, SB525334, SD208, and any combinations thereof. In another embodiment, DE cell is sequentially exposed to small molecular inhibitors to suppress posterior endoderm fate and induce proximal endoderm fate. In a particular embodiment, the small molecular inhibitors inhibit BMP/TGF signaling, such as dorsomorphin, Noggin, A83-01, DMH-1, D4476, GW788388, LY364947, RepSox, SB431542, SB505124, SB525334, SD208, and any combinations thereof. In another particular embodiment, the small molecular inhibitors inhibit TGF/WNT signaling, such as IWR-1, Noggin, CCT036477, IWP2, demethoxy curcumin, FH535 A83-01, D4476, GW788388, LY364947, RepSox, SB431542, SB505124, SB525334, SD208, and any combinations thereof. In another embodiment, the DE cells are first exposed to small molecule inhibitors that inhibit BMP/TGF signaling then exposed to small molecule inhibitors that inhibit TGF/WNT signaling.

The DE cells can be cultured in the presence of small molecule inhibitors that inhibit BMP/TGF signaling for at least about 6 hours. The DE cells can be cultured for at least about 12 hrs, 16 hrs, 20 hrs, 24 hrs, 30 hrs, 36 hrs, 48 hrs, 3 days, 4 days, 5 days, 6 days, 7 days, 8 days, 9 days, 10 days or more with the small molecule inhibitors that inhibit BMP/TGF signaling. In one embodiment, the DE cells are cultured with small molecule inhibitors that inhibit BMP/TGF signaling in the range of about 2 days to about 10 days. In one embodiment, the DE cells are cultured with small molecule inhibitors that inhibit BMP/TGF signaling in the range of about 2 days to about 7 days.

The DE cells can be cultured in the presence of small molecule inhibitors that inhibit TGF/WNT signaling for at least about 6 hours. The DE cells can be cultured for at least about 12 hrs, 16 hrs, 20 hrs, 24 hrs, 30 hrs, 36 hrs, 48 hrs, 3 days, 4 days, 5 days, 6 days, 7 days, 8 days, 9 days, 10 days, or more with the small molecule inhibitors that inhibit TGF/WNT signaling. In one embodiment, the DE cells are cultured with small molecule inhibitors that inhibit TGF/WNT signaling in the range of about 2 days to about 10 days. In one embodiment, the DE cells are cultured with small molecule inhibitors that inhibit TGF/WNT signaling in the range of about 2 days to about 7 days.

Anterior Foregut Endoderm Cells

The AFE cells differentiated from the DE cells express an array of anterior foregut endoderm cell markers. An example of anterior foregut endoderm cell marker includes, but is not limited to, NKX2.1.

NKX2.1 is a protein which in humans is encoded by the NKX2-1 gene. Exemplary NKX2.1 sequences include human NKX2.1 sequence found at GenBank Accession No. NM_001079668 or NP_001073136, or a fragment thereof, and the mouse NKX2.1 sequence found at NM_001146198 or NP_001139670, or a fragment thereof. In one embodiment, the AFE cell express NKX2.1.

The method of differentiating the iPS cell into the airway epithelial cell also includes culturing the AFE cell to induce differentiation of the AFE cell into the airway epithelial cell. In one embodiment, the AFE cells are cultured in the presence of serum. In another embodiment, the AFE cells are cultured in the presence of a high concentration of retinoic acid. In yet another embodiment, the AFE cells are cultured in the presence of a cytokine cocktail. In a particular embodiment, cytokine cocktail inhibits the WNT pathway. Examples of cytokines that inhibit the WNT pathway include, but are not limted to, IWR-1, PD98059, BMP4, BMP7, and other WNT antagonists, and any combinations thereof.

The AFE cells are cultured in the presence of a high concentration of retinoic acid to induce differentiation. The high concentration of retinoic acid can be in the range of about 0.1 µM to about 2.0 µM. The high concentration of retinoic acid can be about 0.1 µM, 0.2 µM, 0.3 µM, 0.4 µM, 0.5 µM, 0.6 µM, 0.7 µM, 0.8 µM, 0.9, 1.0 µM, 1.1 µM, 1.2 µM, 1.3 µM, 1.4 µM, 1.5 µM, 1.6 µM, 1.7 µM, 1.8 µM, 1.9 µM, 2.0 µM, and any concentration in between.

The AFE cells can be cultured in the presence of a high concentration of retinoic acid for at least about 6 hours. The AFE cells can be cultured for at least about 12 hrs, 16 hrs, 20 hrs, 24 hrs, 30 hrs, 36 hrs, 48 hrs, 3 days, 4 days, 5 days, 6 days, 7 days, 8 days, 9 days, 10 days, or more in the high concentration of retinoic acid. In another embodiment, the AFE cells are cultured in the high concentration of retinoic acid for at least about 3 days. In one embodiment, the AFE cells are cultured with the high concentration of retinoic acid in the range of about 2 days to about 10 days. In one embodiment, the AFE cells are cultured with the high concentration of retinoic acid in the range of about 2 days to about 7 days.

Lung Tissue Engineering

The present invention also provides an engineered three-dimensional lung tissue and methods of making the three dimensional lung tissue. In one aspect, an engineered three-dimensional lung tissue is described. The engineered lung includes airway epithelial cells. The airway epithelial cells express airway cell surface markers, such as Clara cell secretory protein (CCSP), cytokeratin 5 (KRT5), and FOXJ1; and are capable of proliferation in culture without loss of the airway cell markers. Thus, the invention provides an alternative source of donor lung tissue to treat end stage disease with engineered lungs.

In another aspect, a method of engineering a three-dimensional lung tissue is described. The method includes differentiating a population of induced pluripotent stem (iPS) into airway epithelial cells, wherein the airway epithelial cells express airway cell surface markers: Clara cell secretory protein (CCSP), cytokeratin 5 (KRT5), and FOXJ1; and are capable of proliferation in culture without loss of the airway cell markers. The method also includes seeding the airway epithelial cells onto a three-dimensional scaffold, such as a scaffold comprising matrigel. Seeding the airway epithelial cells onto the three-dimensional scaffold allows the airway epithelial cells to form an organoid structure. Scaffolds known in the art are useful with the invention. Scaffolds can include, but are not limited to, decellularized tissue, and synthetic/natural or combinations of synthetic and natural polymeric scaffolds. In one embodiment, the three-dimensional scaffold comprises matrigel. Method of scaffold production can include those described in U.S. application Ser. Nos.: 2013/0013083 and 2012/0064050, which are incorporated by reference in their entireties.

Methods of Treatment

The airway epithelial cells derived from iPS cells and engineered lung tissues including such cells have use in vivo for treatment of subjects. The present invention includes methods for treating a respiratory disorder in a subject. As described herein, in one aspect a method includes improving, treating or relieving a symptom of a respiratory disorder in a subject in need thereof. The method also includes differentiating an induced pluripotent stem (iPS) into an airway epithelial cell, wherein the airway epithelial cells express airway cell surface markers, Clara cell secretory protein (CCSP), cytokeratin 5 (KRT5), and FOXJ1, and are capable of proliferation in culture without loss of the airway cell markers and administering the airway epithelial cells in an amount effective to treat the respiratory disorder in the subject.

The methods of treating subjects can further include administering the airway epithelial cells derived from iPS cells or implanting an engineered tissue including airway epithelial cells derived from iPS cells, where administering or implanting results in an improvement, treatment or relief a symptom of a respiratory disorder in the subject. The improvement, treatment or relief can be any change in the respiratory disorder or a symptom of the respiratory disorder that can be detected using the natural senses or man-made devices.

The respiratory disorders that can be treated using the methods of the present invention are diseases or conditions that are physically manifested in the respiratory tract including, but not limited to, cystic fibrosis, respiratory distress syndrome, acute respiratory distress syndrome, pulmonary tuberculosis, cough, bronchial asthma, cough based on increased airway hyperreactivity (bronchitis, flu syndrome, asthma, obstructive pulmonary disease, and the like), flu syndrome, anti-cough, airway hyperreactivity, tuberculosis disease, asthma (airway inflammatory cell infiltration, increased airway hyperresponsiveness, bronchoconstriction, mucus hypersecretion, and the like), chronic obstructive pulmonary disease, emphysema, pulmonary fibrosis, idiopathic pulmonary fibrosis, cough, reversible airway obstruction, adult respiratory disease syndrome, pigeon fancier's disease, farmer's lung, bronchopulmonary dysplasia, airway disorder, emphysema, allergic bronchopulmonary aspergillosis, allergic bronchitis bronchiectasis, occupational asthma, reactive airway disease syndrome, intersitial lung disease, parasitic lung disease, and the like. In one embodiment, the respiratory disorder is cystic fibrosis.

Advantageously, the compositions and methods of the invention represent an improvement over prior art methods. Preferably the compositions for use in treating a respiratory disorder include airway epithelial cells derived from iPS cells, as described elsewhere herein.

The invention also encompasses the use of a pharmaceutical formulation of the invention to practice the methods of the invention. Such a pharmaceutical formulation may be provided in a form suitable for administration to a subject, and may be comprise one or more pharmaceutically acceptable carriers, one or more additional ingredients, or some combination of these.

Pharmaceutical formulations that are useful in the methods of the invention may be suitably developed for inhalational, oral, parenteral, pulmonary, intranasal, intravenous or another route of administration. Other contemplated formulations include projected nanoparticles, liposomal preparations, and immunologically-based formulations. The route(s) of administration will be readily apparent to the skilled artisan and will depend upon any number of factors including the type and severity of the disease being treated, the type and age of the veterinary or human patient being treated, and the like.

The pharmaceutical formulations described herein may be prepared by any method known or hereafter developed in the art of pharmacology. In general, such preparatory methods include the step of bringing the cells into association with a carrier or one or more other accessory ingredients, and then, if necessary or desirable, shaping or packaging the product into a desired single- or multi-dose unit.

In one embodiment, the cells of the invention are formulated using one or more pharmaceutically acceptable excipients or carriers. In one embodiment, the pharmaceutical formulations of the cells of the invention include a therapeutically effective amount of the cells of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., N.J.).

Administration/Dosing

In the clinical settings, delivery systems for the cells can be introduced into a patient by any of a number of methods, each of which is familiar in the art. For instance, a pharmaceutical formulation of the cells can be administered by inhalation or systemically, e.g. by intravenous injection.

In one exemplary implementation, the pharmaceutical formulation of the cells can be administered directly by injection into a pulmonary tissue. U.S. Ser. No. 10/914,829 describes a protocol for direct injection.

The regimen of administration may affect what constitutes an effective amount. The therapeutic formulations may be administered to the patient either prior to or after the manifestation of symptoms associated with the disease or condition. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the cells of the present invention to a subject, preferably a mammal, more preferably a human, may be carried out using known procedures, at dosages and for periods of time effective to treat a disease or condition in the patient. An effective amount of the cells necessary to achieve a therapeutic effect may vary according to factors such as the extent of implantation of the cells administered; the time of administration; the duration of administration; other drugs, compounds or materials used in combination with the cells; the state of the disease or disorder; age, sex, weight, condition, general health and prior medical history of the subject being treated; and like factors well-known in the medical arts. Dosage regimens may be adjusted to provide the optimum therapeutic response. For example, several divided doses may be administered daily or the dose may be proportionally reduced as indicated by the exigencies of the therapeutic situation. One of ordinary skill in the art would be able to study the relevant factors and make the determination regarding the effective amount of the cells without undue experimentation.

Actual dosage levels of the cells in the pharmaceutical formulations of this invention may be varied so as to obtain an amount of the cells that are effective to achieve the desired therapeutic response for a particular subject, composition, and mode of administration, without being toxic to the patient.

Routes of Administration

Routes of administration of the cells of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable formulation of the cells and dosages include, for example, dispersions, suspensions, solutions, beads, pellets, magmas, creams, pastes, plasters, lotions, discs, suppositories, liquid sprays for nasal or oral administration, aerosolized formulations for inhalation, compositions and formulations for intravesical administration and the like.

It should be understood that the formulations and compositions that would be useful in the present invention are not limited to the particular formulations set forth in the examples. The following examples are put forth so as to provide those of ordinary skill in the art with a complete disclosure and description of how to make and use the cells, differentiation methods, engineered tissues, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

The Materials and Methods used in the performance of the experiments disclosed herein are now described Cultivation of Human iPS Cells The human iPS cell lines, reprogrammed iPS cells using lentiviral (clone C2) utilized in the current study was provided by Prof. James A Thomson, Department of Anatomy, University of Wisconsin-Madison, Madison, Wis. Clone C2 were generated by lentiviral transduction of isolated human skin fibroblasts with OCT-4, SOX2, Nanog and lin28 gene. CF-iPS cells were provided by Prof. Darrell N Kotton and generated from dermal fibroblasts isolated from a cystic fibrosis patient skin sample. CF-iPS cells was transgene free generated by single lentiviral vector. These induced pluripotent human stem cells were already characterized in the Thomson and Kotton lab. They have normal karyotypes, express telomerase activity, express cell surface markers and genes that characterize human ES cells, and maintain the developmental potential to differentiate into advanced derivatives of all three primary germ layers. These two lines of iPS cells exhibited morphology indistinguishable from hESCs such as H9 and can be maintained indefinitely on mouse embryonic fibroblast feeders or Matrigel. Both human iPS cells were cultured and maintained as described previously by the Thomson laboratory. Briefly, iPS cells were propagated on irradiated mouse embryonic fibroblast (MEF) feeder layers in DMEM-F12 media and 20% of knock out serum replacement supplemented with 4 ng/ml bFGF, 1 mM Glutamine, 1% mM non-essential amino acids and 0.1 mM β-mercapthoethanol at 37° C., 5% CO2 and 90-95% humidity, with medium change every day. Undifferentiated iPS cells were passaged every 4-5 days onto fresh feeders by mechanical dissociation using a Stem Cell Cutting Tool (VWR).

In Vitro Differentiation of iPS Cells to Airway Epithelial Cells iPS cells were first differentiated towards definitive endoderm (DE). DE cells were initiated under conditions described previously. Briefly, iPS cells were cultured in RPMI 1640 medium supplemented with 100 ng/ml activin A, 2 mM L-glutamine and 1% antibiotic-antimycotic for 48 hours. Then, 1xB27 supplement and 0.5 mM sodium butyrate were added into the same medium and iPS cells were cultured in this medium for 3 days with daily medium changes.

Subsequently, the DE cells were trypsinized and replated on human ECM protein coated plates and were differentiated to anterior foregut endoderm (AFE) by exposing them sequentially between days d5 to d7 to combinations of the small molecule inhibitors in IMDM with 10% FBS, 2 mM L-glutamine, 1 mM nonessential amino acids, 1% antibiotic-antimycotic. See FIG. 1.

Then AFE cells were maintained in lung endoderm differentiation medium consisting of IMDM with 20% FBS, 2 mM L-glutamine, 1 mM nonessential amino acids, 1% antibiotic-antimycotic, retinoic acid (0.5 µM), bFGF (10 ng/ml), BMP4 (10 ng/ml), Wnt3a (100 ng/ml), and KGF (10 ng/ml each) for 5 days. The growth factor combination were then switched to BMP7 (10 ng/ml), KGF (10 ng/ml), high concentration of retinoic acid (1 µM), RA-supplemented B27, IWR-1(100 nM), (WNT antagonist) PD98059 (1 µM) (MAPK antagonist) for 3 days.

Beginning on day 16 cells were differentiated further to airway epithelial cells in the same basal media supplemented with IWR-1(50 nM), high RA (1 µM), BMP7 (10 ng/ml), KGF (10 ng/ml), EGF (10 ng/ml), dexamethasone (50 nM), butyrylcAMP (0.1 mM) and isobutylmethylxanthine (0.1 mM) for 12 days. As an alternative, the DE cells were differentiated directly, without splitting, using the same medium mentioned above. At day 28, cells were split with trypsin and reseeded on collagen VIII coated plates in BEGM™ Bronchial Epithelial Cell Growth Medium—from Lonza until use.

Real Time Quantitative RT-PCR

Total RNA was extracted from iPS cells and iPS cell-derived airway epithelium cells using the RNeasy Mini Kit from Qiagene following the manufacturer's instructions. First-strand complementary DNA (cDNA) was synthesized with random hexamers as primers, using SuperScript First-Strand Synthesis System according to manufacturer's protocol (Invitrogen). An equal volume mixture of the products was used as templates for PCR amplification. Reactions were performed in a 25 µl volume with iQ™ SYBR Green Supermix (Bio-Rad) and 200 nM each of forward and reverse primers shown using iCyler and iQ software (Bio-Rad). Each sample was run in triplicate. PCR conditions included an initial denaturation step of 4 min at 95° C., followed by 40 cycles of PCR consisting of 15 s at 95° C., 30 s at 60° C., and 30 s at 72° C. Average threshold cycle (Ct) values from the triplicate PCR reactions for a gene of interest (GOI) were normalized against the average Ct values for GAPDH from the same cDNA sample. Fold change of GOI transcript levels between sample A and sample B equals $2^{-\Delta\Delta Ct}$, where $\Delta Ct=Ct_{(GOI)}-Ct_{(GAPDH)}$, and $\Delta\Delta Ct=\Delta Ct_{(A)}-\Delta Ct_{(B)}$.

Flow Cytometry and Immunochemistry Analysis

Before differentiation and during the induction of DE and AFE and differentiation towards airway epithelium, the cells were analyzed by immunochemistry and/or flow cytometry at different time points. iPS cells and differentiated cells were fixed in 4% paraformaldehyde in PBS for 20 min, permeabilized with 0.1% Triton X-100 in PBS for 15 min at room temperature (RT), blocked in 3% BSA in PBS for 60 min at RT, and then incubated in primary antibody overnight at 4° C., secondary antibody for 2 h at RT.

For flow cytometry, cells were fixed with the fixation solution from the Fixation/Permeabilization kit (BD Biosciences), and stained with primary and detection antibodies as described by the manufacturer. Briefly cells were dissociated into single-cell suspensions by incubation with 0.25% trypsin for 2 min. The dissociated cells were resuspended ($0.5 \times 10^6$ cells) in 250 µl of fixation/permeabilization solution, kept on ice for 20 min, and washed twice with Perm/Wash buffer. After blocking with blocking solution for 30 min on ice, the cells were incubated with corresponding primary antibody in the blocking solution for 30 min on ice. The cells were resuspended in 350 µl of Perm/Wash buffer after incubation with corresponding conjugated secondary for 30 min on ice, washed twice, and analyzed by flow cytometry.

Statistical Analyses

All statistical analyses were done with the software Origin (OriginLab, Northampton, Mass.). The data were expressed as mean±s.e.m. (standard error of measurement). T-tests were performed to evaluate whether two groups were significantly different from each other. p values less than 0.05 (two-tailed) was considered statistically significant. All error bars represent±SEM.

Organoid Formation

Airway progenitor cells at day 15 were cultured in Matrigel in air-liquid phase condition in airway epithelial cells differentiated in IMDM media supplemented with high RA (1 µM), BMP7 (10 ng/ml), KGF (10 ng/ml), EGF (10 ng/ml), dexamethasone (50 nM), butyrylcAMP (0.1 mM) and isobutylmethylxanthine (0.1 mM) for 30 days. Cells were fixed with the fixation solution from the Fixation/Permeabilization kit (BD Biosciences), and stained with primary antibodies for airway epithelial cells, P63 and NKX2.1 and detection antibodies as described by the manufacturer.

The Results of the experiments disclosed herein are now described.

The lung has a complex three-dimensional structure that features major differences in the composition of the epithelium along its proximo-distal axis. The luminal epithelium (trachea and primary bronchi) is largely composed of ciliated cells, neuroendocrine (NE) and Clara-like cells. The latter produce secretoglobins, CCSP. In the more distal airways (small bronchi and bronchioles), Clara cells predominate over ciliated cells and there are more NE cells than in the trachea. The most distal region of the lung is organized into a complex system of alveoli that are comprised of two primary epithelial cells types: Type I (ATI) and Type II (ATII) epithelial cells. ATI line the majority of the alveolus in the lung (covering up to 95% of the alveolar surface area) and are primarily responsible for gas-exchange, while ATII cells secrete alveolar surfactants and are primarily cuboidal in shape. A step-wise differentiation method to generate definitive endoderm (DE), anterior foregut endoderm (AFE), and subsequently, a relatively homogeneous population of human alveolar type II cells from human iPS cells has been previously described (Ghaedi, et al., JCI 2012). In the work described herein, a stepwise differentiation approach that mimics the timing and coordination of the signaling pathways that guide airway epithelial development is employed. Using an unique strategy, functional airway epithelial cells from human pluripotent stem cells with high efficacy were generated.

Induction of Human iPS cells into Anterior Fore gut Endoderm and Lung Endoderm Cells. The embryonic respiratory system, distal to the trachea, originates from lung buds on the anterior ventral aspect of the definitive endoderm (DE) at embryonic day 9.5 in the mouse or week 4 in humans differentiating into many kinds of specialized epithelial cells.

Figure 2A:
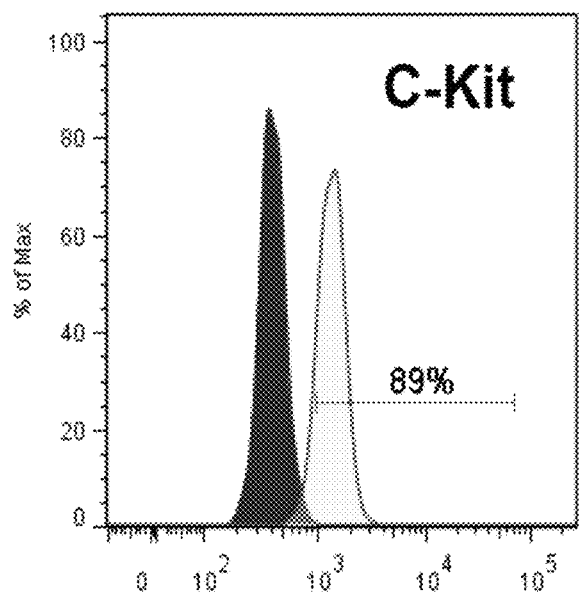
FIG. 2A shows flow cytometric analysis of the cell population derived from iPS cells at day 5 expressing c-kit.
Figure 2B:
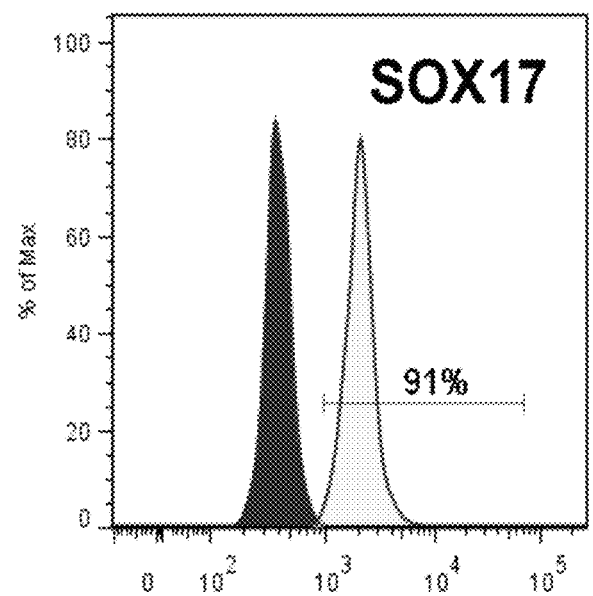
FIG. 2B shows flow cytometric analysis of the cell population derived from iPS cells at day 5 expressing FOXA2.
Figure 2C:
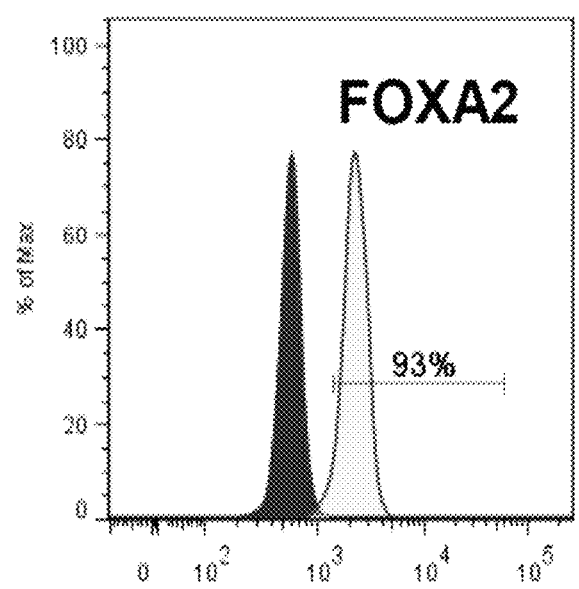
FIG. 2C shows flow cytometric analysis of the cell population derived from iPS cells at day 5 expressing SOX17.
Figure 2D:
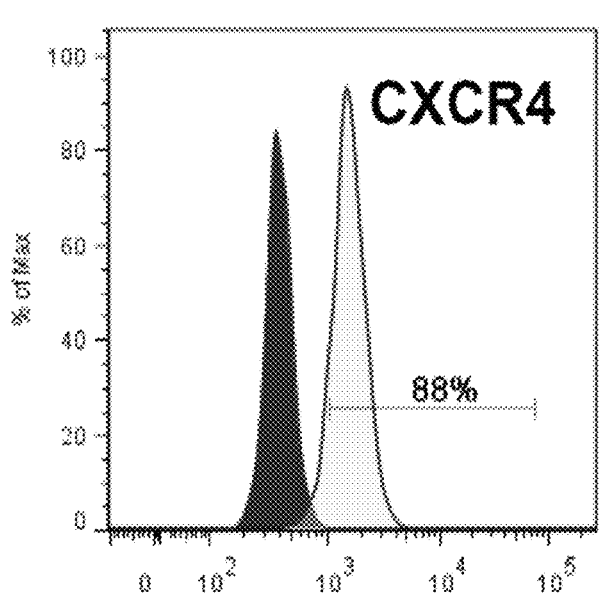
FIG. 2D shows flow cytometric analysis of the cell population derived from iPS cells at day 5 expressing CXCR4 in clone C1.

Human iPS cells were differentiated to DE cells using serum free conditions (FIG. 1). By exposing iPS cells to saturating concentrations of activin A, greater than 85% endodermal cells were generated. Flow cytometric analysis showed the cell population derived from iPS cells at day 5 expresses a high percentage of markers associated with this germ layer. 89% of cells were positive for c-kit (FIG. 2A), 91% positive for SOX17 (FIG. 2C), 93% positive for FOXA2 (FIG. 2B), and 88% of the cells expressed the endoderm surface marker CXCR4 (FIG. 2D) in clone C1.

Although the definitive endoderm cells derived in this manner have been presumed to be broadly multipotent, several studies have shown the most anterior foregut endodermal lineages, such as thymus, thyroid, and lung epithelia, have been difficult to derive from these progenitors. Directed differentiation to alveolar epithelium should proceed by generation of definitive endoderm (DE), followed by patterning into anterior foregut endoderm (AFE).

Therefore, in the second step, the DE cells were further differentiated to AFE. The DE cells were dissociated, replated on Human ECM-coated plates and cultured in AFE differentiation media for 2 days. The choice of ECM proteins was driven from a previous study which showed that DE cells cultured on human ECM protein surfaces containing a mixture of extracellar protein matrix (collagens, laminin, fibronectin, tenascin, elastin, and a number of proteoglycans and glycosaminoglycans), attached faster and resulted in higher number of NKX2.1$^+$ compared with DE cells cultured on other ECM proteins.

Experiments on mouse and human ES and iPS clearly have demonstrated that dual inhibition of activin A/nodal and TGF-$\beta$/BMP signaling in iPS cell-derived definitive endoderm is required to quantitatively generate anterior foregut endoderm. In a previous attempt, the application of Noggin (inhibitor of BMP signaling) and SB141524 (the TGF-$\beta$ signaling inhibitor) for 2 days to DE cells suppressed a posterior endoderm fate (CDX2$^+$) in favor of an anterior endoderm fate (SOX2$^+$) and yielded an enriched population of cells with strong expression of markers associated with the AFE phenotype.

Figure 3A:
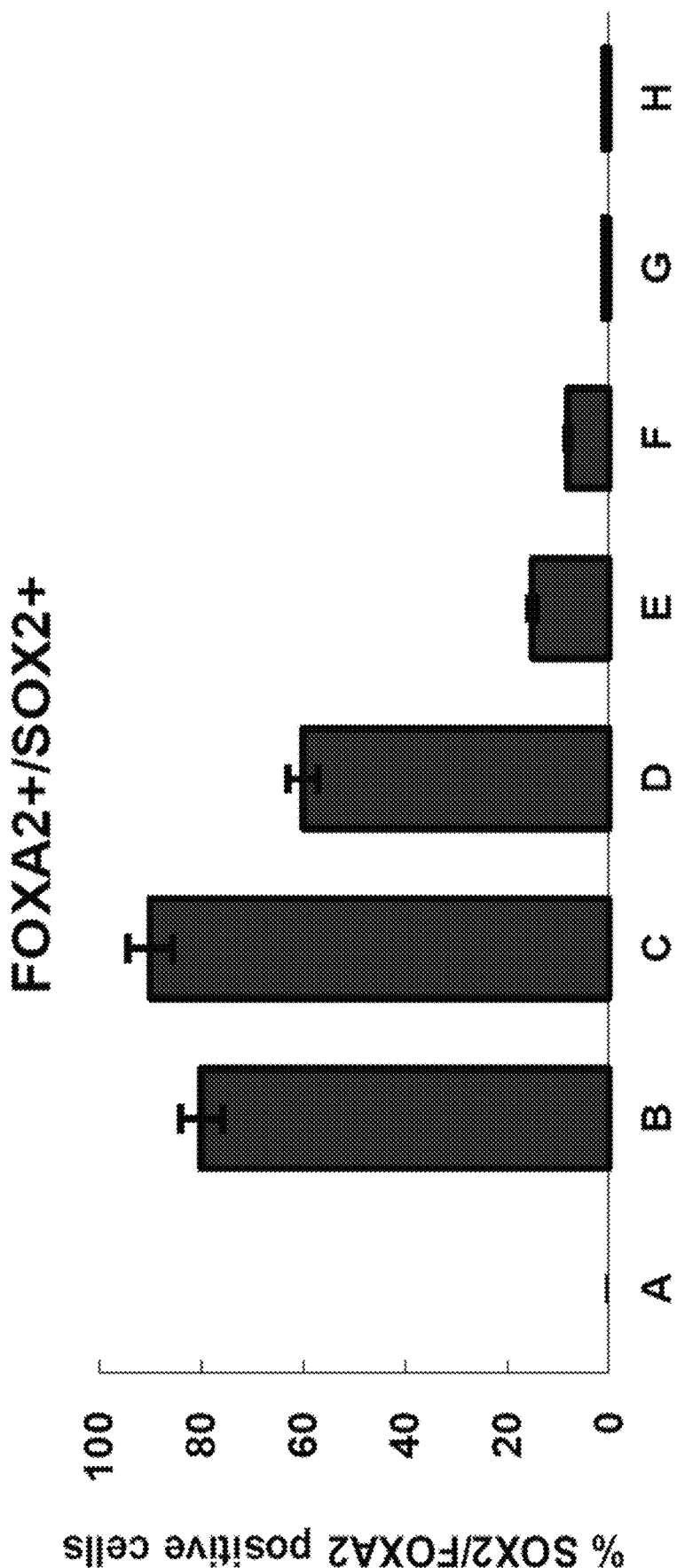
FIG. 3A shows the effect of agonists and antagonists during AFE differentiation on FOXA2/SOX2 expression.
Figure 3B:
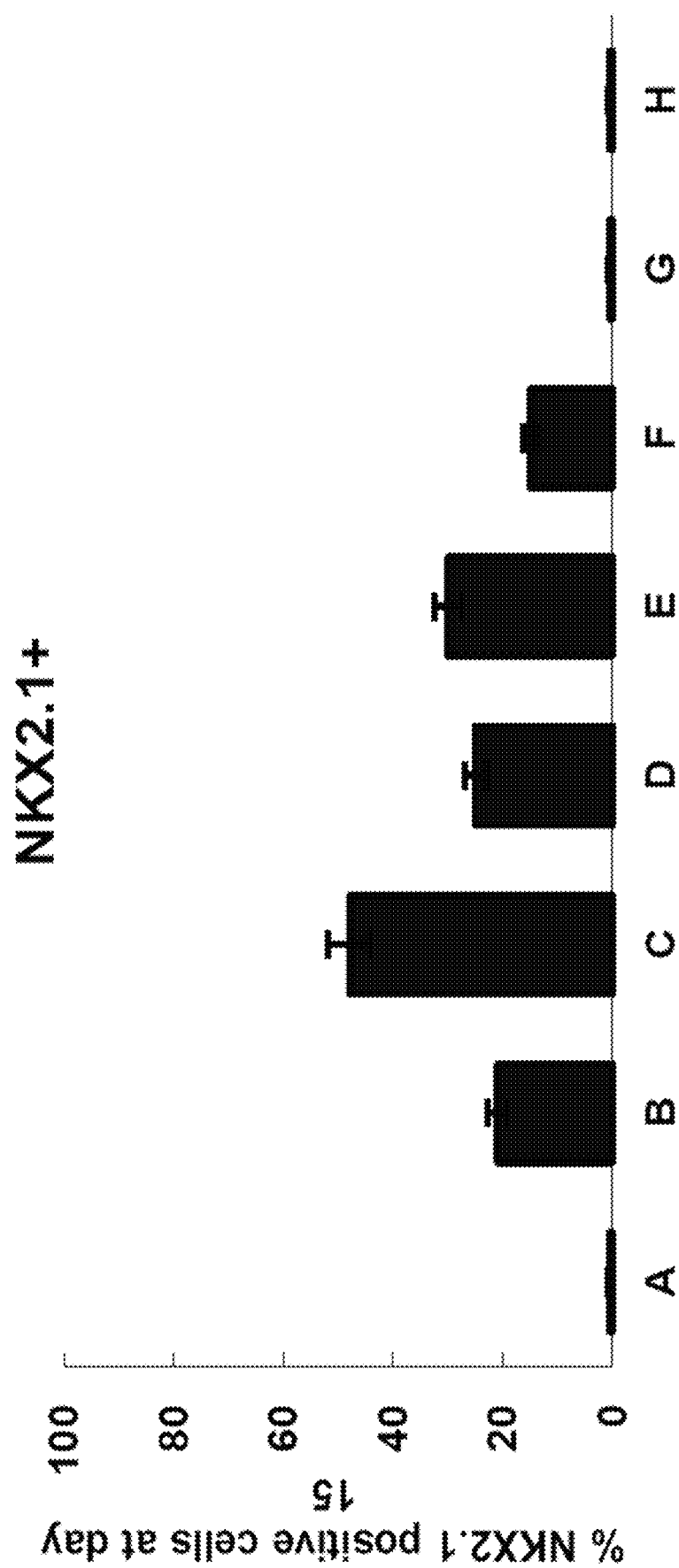
FIG. 3B shows the effect of agonists and antagonists during AFE differentiation on NKX2.1 expression.

To increase the number of NKX2.1$^+$FOXA2$^+$ progenitor cells, modifications were made to prior approaches to produce AFE from DE cells. Sneock and colleagues have shown sequential inhibition of BMP/TGF followed by TGF and Wnt signaling pathway inhibition give better AFE differentiation from DE cells (Huang S X, et al., Nat Biotechnol., 2013 Dec. 1. doi: 10.1038/nbt.2754). To promote AFE identity, DE cells were then exposed sequentially between Days 6 to 8 to different combinations of BMP4/TGF$\beta$ and Wnt agonist and antagonists as listed in Table 1. The ability to increase the NKX2.1$^+$, FOXA2$^+$SOX2$^+$ and NKX2.1$^+$ FOXA2$^+$ progenitor cell numbers was examined. The effect of the agonists and antagonists listed in Table 1 during AFE differentiation on FOXA2/SOX2 and NKX2.1 expression are shown in FIGS. 3A and 3B, respectively.

TABLE 1

List of BMP4/TGF$\beta$ and Wnt agonists and antagonists sequentially added between days 6 to 8.

| Conditions | Agonist/Antagonist 5-6 Days | Concentration | Agonist/Antagonist 6-7 Days | Concentration |
|---|---|---|---|---|
| A | Medium | N/A | Medium | N/A |
| B | Noggin/SB | 200 ng/10 mM | Noggin/SB | 200 ng/10 mM |
| C | Dorsomorphin, SB | 10 µM/10 mM | IWP2, SB | 10 µM/10 mM |
| D | A-83-01, Dorsomorphin | 500 nM/10 µM | IWP2, SB | 10 µM/10 mM |
| E | Dorsomorphin, SB | 10 µM/10 mM | Dorsomorphin, SB | 10 µM/10 mM |
| F | IWP2, SB | 10 µM/10 mM | IWP2, SB | 10 µM/10 mM |
| G | Activin A | 100 ng | Activin A | 100 ng |
| H | BMP4 | 10 ng | BMP4 | 10 ng |

Previous studies showed that FGF, BMP4 family members, KGF and WNT3a provide signals during embryogenesis for patterning into lung endoderm. BMP4 signaling is required for lung specification and an increase in bFGF and WNT concentration increases NKX2.1$^+$ immature lung progenitors. To specify lung cell fate, after day 7 the medium was switched to lung endoderm differentiation medium containing bFGF (10 ng/ml), BMP4 (10 ng/ml), Wnt3a (100 ng/ml), and KGF (10 ng/ml) for 5 days. The number of FOXA2$^+$SOX2$^+$ anterior endoderm cells between different conditions at day 7 was compared. The numbers of cells double positive for FOXA2$^+$ SOX2$^+$ anterior endoderm cells were quantified out of the total FOXA2$^+$ endoderm cells by flow cytometry. The results indicated that blocking of BMP4/TGFB and Wnt signaling in DE cells increased the number of FOXA2$^+$SOX2$^+$ anterior endoderm cells compared to medium alone. This increase was more pronounced when cells were exposed sequentially to combinations of dorsomorphin/SB431542 (inhibitor of BMP/TGFβ) and IWP2/SB431542 (inhibitor of WNT/TGF-β) compared to the combination of other inhibitors (FIG. 3A).

NKX2.1$^+$ is the earliest marker of cells that distinguish future lung from other derivatives of the foregut endoderm. The sequential exposure to BMP/TGFβ and WNT/TGF-β was tested to determine if it rendered iPS cell-DE cells more competent to differentiate into NKX2.1$^+$ endodermal cells. The percentages of NKX2.1$^+$ cells were quantified as percentages of the total cells present. The number of NKX2.1$^+$ cells were higher when DE cells were exposed to the combinations of dorsomorphin/SB431542 (inhibitor of BMP/TGFβ) and IWP2/SB431542 (inhibitor of Wnt/TGF-β) when compared to the combination of other inhibitors (FIG. 3B).

Figure 4:
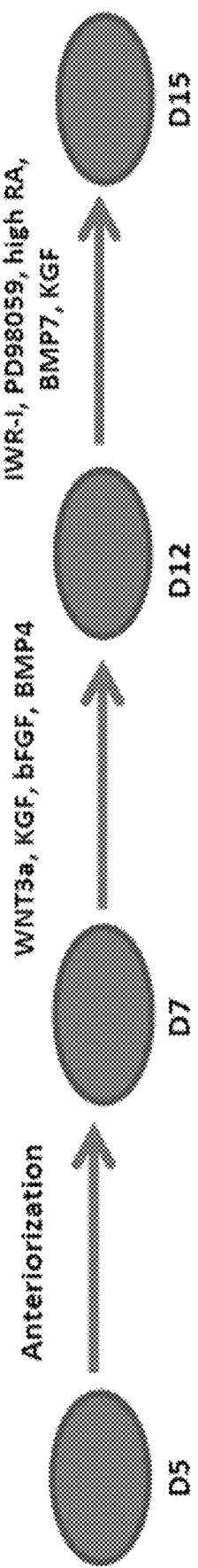
FIG. 4 diagrams the steps of the protocol that were manipulated to differentiate human iPS cells into airway epithelial cells and result in an increase of NKX2.1$^+$ FOXA2$^+$ cells.
Figure 5:
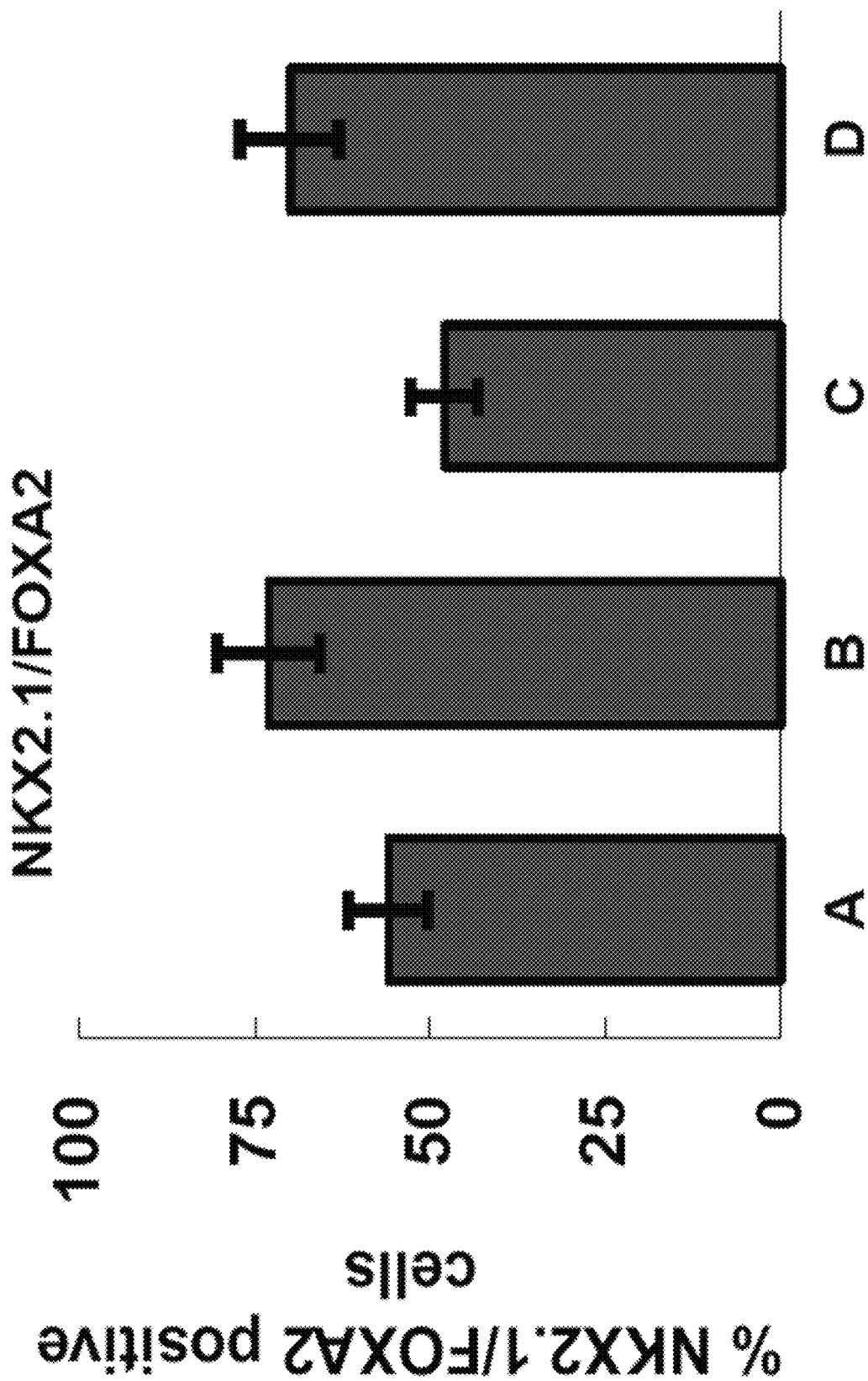
FIG. 5 shows that increase of NKX2.1$^+$FOXA2$^+$ cells at day15 as compared to DE cells exposed to NOGGIN/SB with less than 1% without anteriorization.
Figure 8:
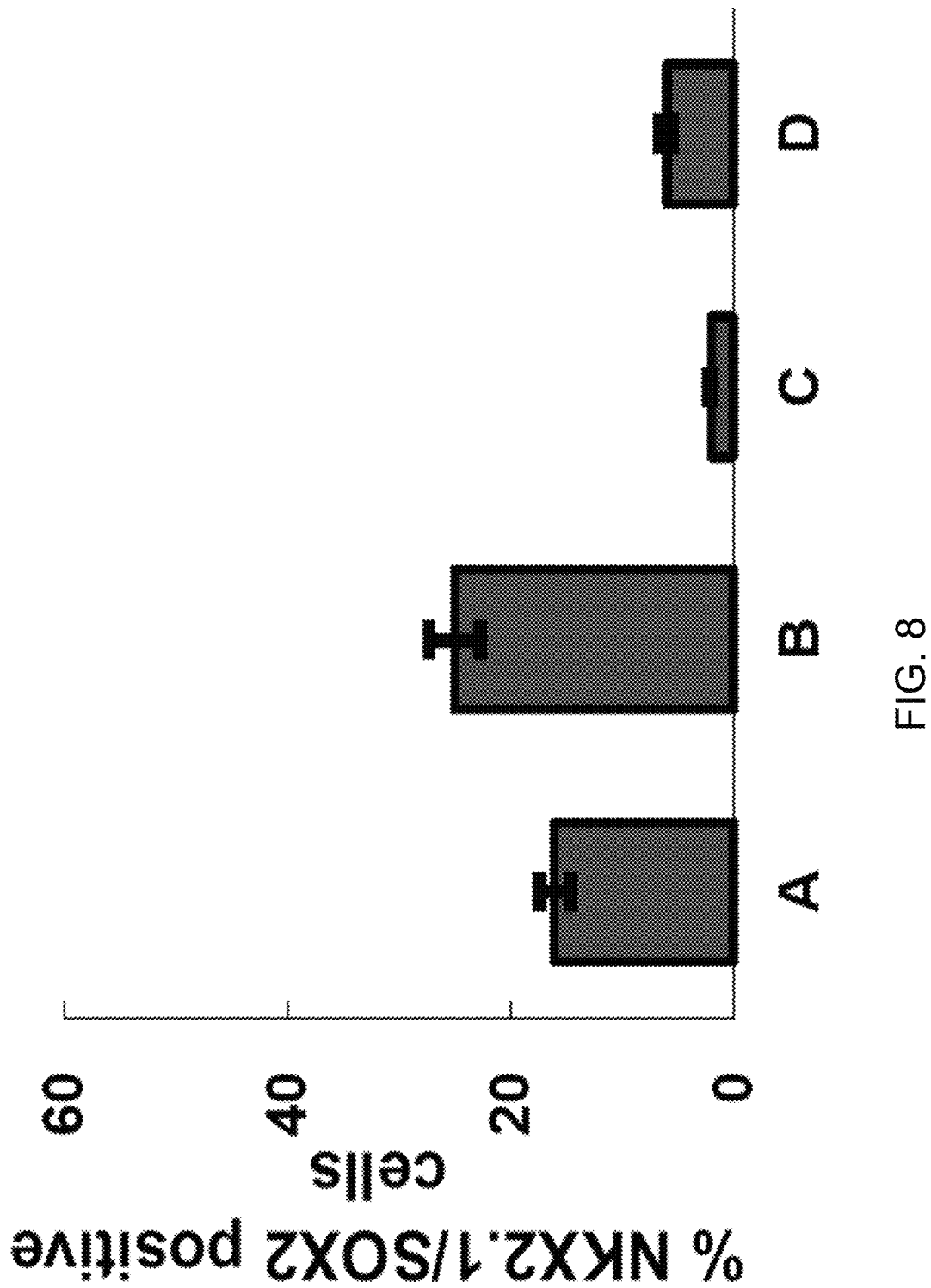
FIG. 8 is a bar graph showing the NKX2.1$^+$/SOX2$^+$ airway progenitor cells made up to about 30% compared to about 1-2% before treatment.

The protocol was further manipulated, see FIG. 4 and Table 2 below, to result in an increase of NKX2.1$^+$FOXA2$^+$ cells at day15, 72.1% as compared to 50% in DE cells exposed to NOGGIN/SB with less than 1% without anteriorization (FIG. 5). All of the ex vivo differentiated NKX2.1$^+$ cells co-stained with FOXA2 (FIGS. 6A-6D) suggested that the NKX2.1$^+$ cells that were differentiated in vitro represented lung endoderm cells. Continuous activin A treatment resulted in rare FOXA2$^+$SOX2$^+$ cells and few NKX2.1$^+$ cells (FIGS. 3A and 3B), suggesting that the optimal duration of activin A exposure was important. No PAX8$^+$ (thyroid marker) and TUJ1 (neuronal marker) cells were detected in the culture (data not shown). All of these results were consistent with the finding that a combination of FGF, BMP4, and WNT signaling, after the sequential blocking of BMP4/TGFB and WNT signaling in DE cells, promoted lineage specification of lung-specific NKX2.1$^+$ progenitor cells from anterior endoderm.

TABLE 2

List of BMP4/TGFβ and Wnt agonist and antagonists sequentially added between days 5-15.

| Conditions | Agonist/Antagonist 5-7 Days | Agonist/Antagonist 7-10 Days | Agonist/Antagonist 10-15 Days |
|---|---|---|---|
| A | SB/Noggin | BMP4, bFGF, WNT3a, KGF | IWR-I, PD98059, high RA, BMP7, KGF |
| B | DSM, SB/IWP2, SB | BMP4, bFGF, WNT3a, KGF | IWR-I, PD98059, high RA, BMP7, KGF |
| C | SB/Noggin | WNT3a, BMP4, FGF10, KGF, RA | WNT3a, BMP4, FGF10, KGF, RA |
| D | DSM, SB/IWP2, SB | WNT3a, BMP4, FGF10, KGF, RA | WNT3a, BMP4, FGF10, KGF, RA |

No markers for any type of mature lung airway epithelial cells such as Mucin1, Mucin5AC (Goblet cells), FOXJ1 (Ciliated cells), and CCSP (Clara cells) were detected at the protein level by immunoflourence staining or PCR (data not shown).

Differentiation of Lung Endoderm Cells Towards Lung Airway Progenitor Cells. Early lung endoderm (NKX2.1$^+$/FOXA2$^+$) is multipotent and its fate is dependent upon signals provided by either the local microenvironment (primarily mesoderm) or by signals that control regional (proximal versus distal) cell fates. The specialization of the airway epithelium occurs in the stalks of the embryonic lung, while alveolar progenitors in the tips differentiate to distal cells, ATII and ATI cells. The NKX2.1$^+$SOX2$^+$ cells in the stalk region are airway progenitor cells that give rise to the mature airway epithelium. In contrast, the distal embryonic lung bud tip express SOX9 and FOXP2 and are capable of producing all of the cell types of the airway and alveoli.

BMP4 is expressed distally, while BMP7 is expressed closer to the airway. Distal bFGF and FGF10 are replaced by proximal KGF (FGF7), while WNT signaling is inhibited in the proximal stalk progenitors and present in the distal tip. SOX2 is a key regulator of bronchiolar lineage specification, which is negatively regulated by canonical WNT signaling Inhibition of WNT and MAPKK/ERK signaling pathways increases the NKX2.1$^+$SOX2$^+$ cell proportion from AFE cells. Retinoic acid (RA) is an important factor for lung bud development, with RA concentration relatively higher in the proximal stalk region than at the distal tip region. High RA signaling prevents distal lung development and favors proximal airway development.

To convert NKX2.1$^+$ lung progenitors into NKX2.1$^+$SOX2$^+$ proximal progenitor cells, the BMP and WNT pathways were regulated to control proximal to distal patterning of the airway tree. At day 12 to enhance proximal airway fate, the growth factor combination was switched to proximal induction medium containing BMP7 (10 ng/ml), KGF (10 ng/ml), high concentration of retinoic acid (1 μM), IWR-1 (100 nM) (WNT antagonist), PD98059 (1 μM) (MAPK antagonist) for 3 days. After 3 days, inhibition of the WNT pathway with IWR-1, PD98059, BMP7, and high RA concentrations was observed. The NKX2.1$^+$/SOX2$^+$ airway progenitor cells made up to about 30% compared to about 1-2% before treatment. (FIGS. 7A-7D and 8)

Figure 9:
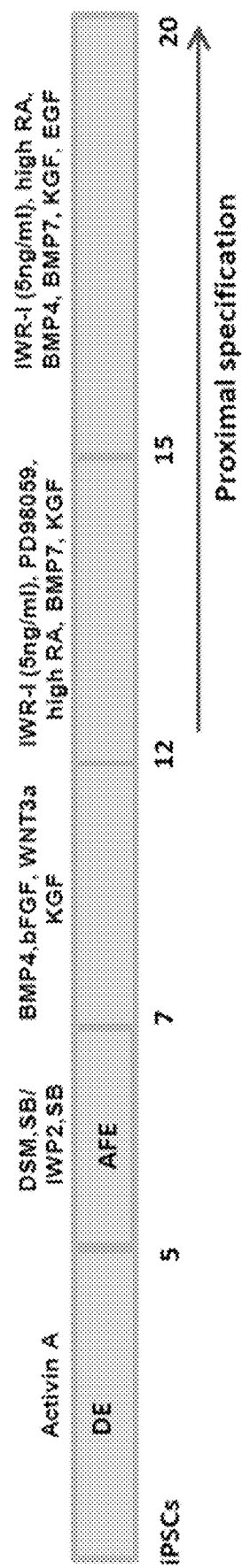
FIG. 9 is a diagram showing airway differentiation and supplements to basal media.
Figure 10A:
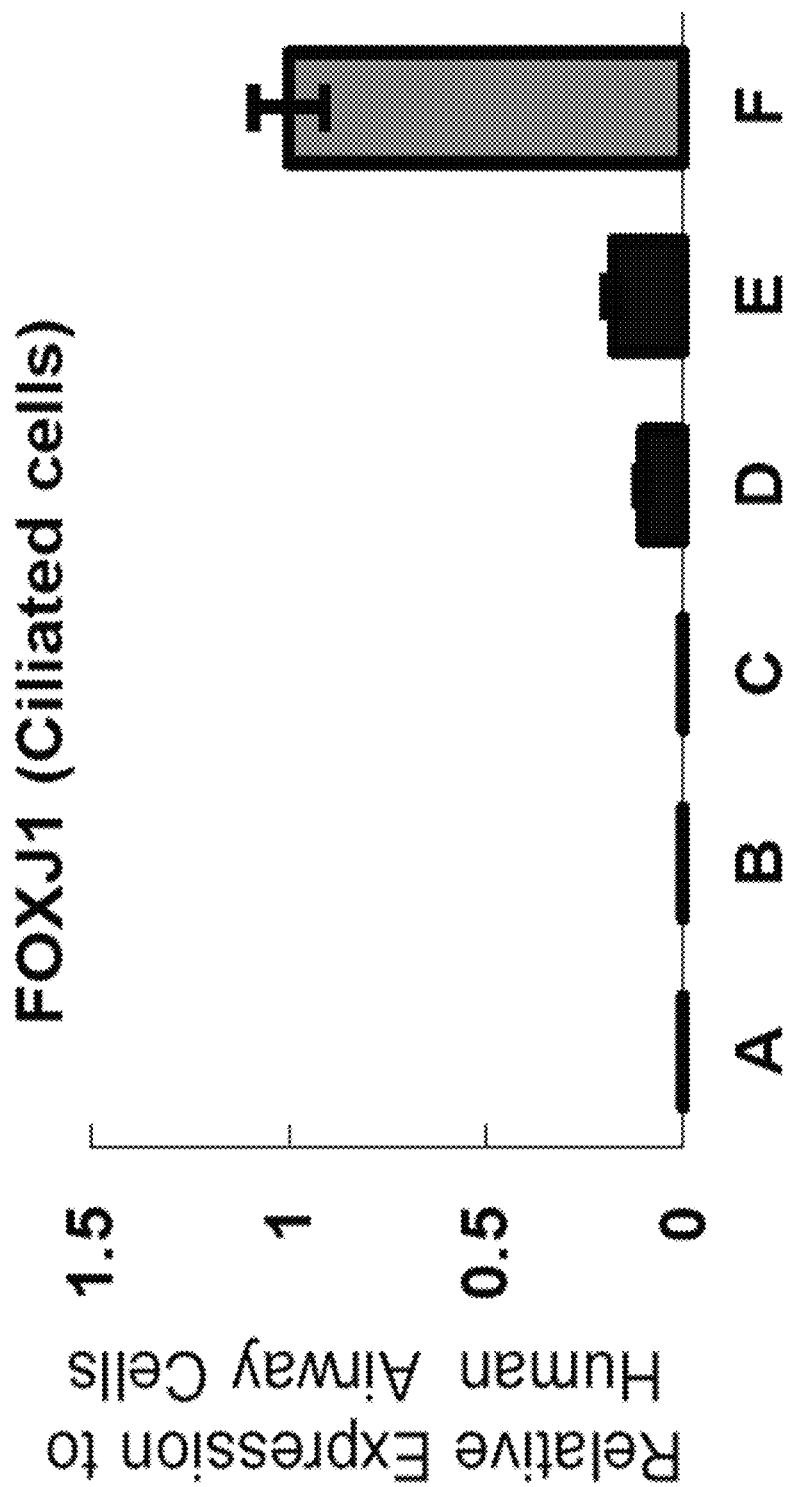
FIG. 10A shows quantitative RT-PCR of FOXJ1 at day 20 results in mature lung airway epithelial cells.
Figure 10F:
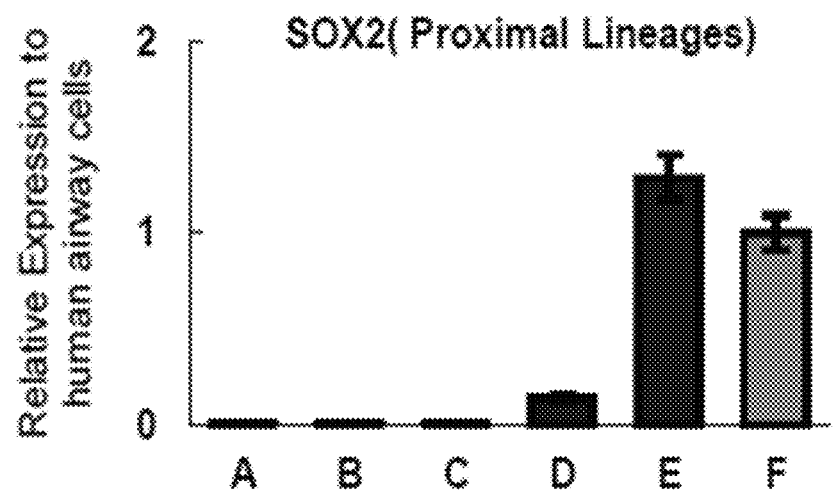
FIG. 10F shows quantitative RT-PCR of SOX2 at day 20 results in mature lung airway epithelial cells.
Figure 10G:
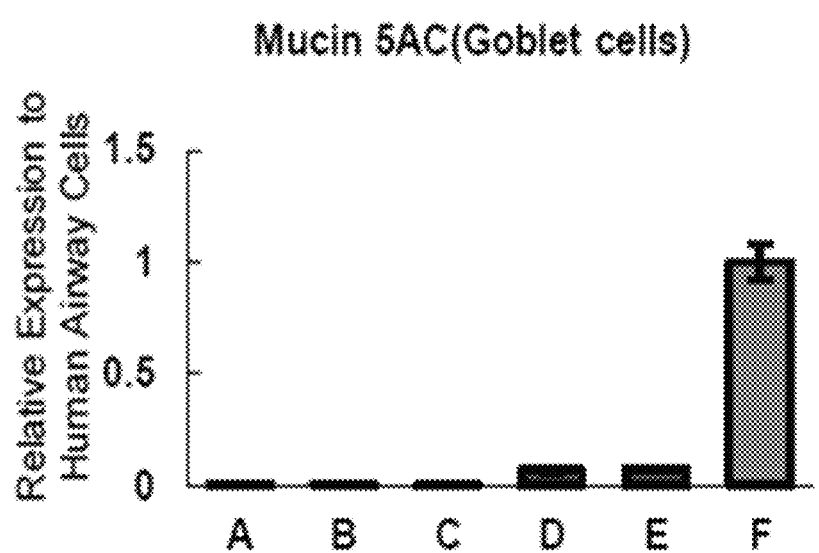
FIG. 10G shows quantitative RT-PCR of Mucin5AC at day 20 results in mature lung airway epithelial cells.

To further promote airway differentiation, progenitor cells at day 15 were cultured in the same basal media supplemented with IWR-1(100 nM), RA (1 μM), BMP4 (10 ng/ml), BMP7 (10 ng/ml), KGF (10 ng/ml), EGF (10 ng/ml) for 12 days. See FIG. 9. Quantitative RT-PCR revealed a relatively modest increase in mature lung airway epithelial cells marker such as FOXJ1 (Ciliated cells)(FIG. 10A), KRT5 (Basal cells)(FIG. 10B), CFTR (FIG. 10C), CCSP or SCGB1A1 (Clara cells)(FIG. 10D), P63 (FIG. 10E), Mucin5AC (Goblet cells)(FIG. 10G), and when compared to SOX2 expression (FIG. 10F), which was highly expressed in cells derived from iPS cells at day 20 of differentiation. See also Table 3.

TABLE 3

A list of agonists and antagonists added to basal media to promote airway differentiation.

| | Treatment | |
|---|---|---|
| Conditions | Agonist/Antagonist (7-10) | Agonist/Antagonist (10-20) |
| A | Undifferentiated human iPS cells | |
| B | Definitive endoderm cells | |
| C | Anterior Foregut endoderm cells | |
| D | BMP4, bFGF, WNT3a, KGF | IWR-I, PD98059, high RA, BMP7, KGF |
| E | WNT3a, BMP4, FGF10, KGF, RA | WNT3a, BMP4, FGF10, KGF, RA |
| F | Human airway cells | |

Figure 11:
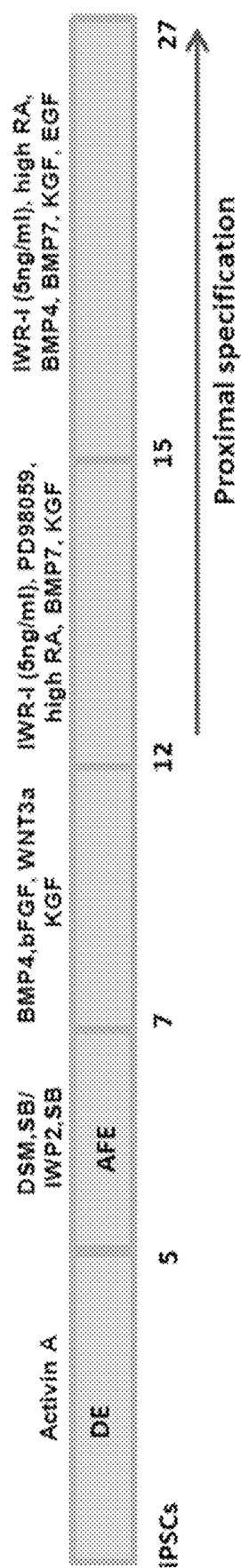
FIG. 11 is a diagram showing at day 27 the growth factors and inhibitor combination to induce airway epithelial differentiation.
Figure 12A:
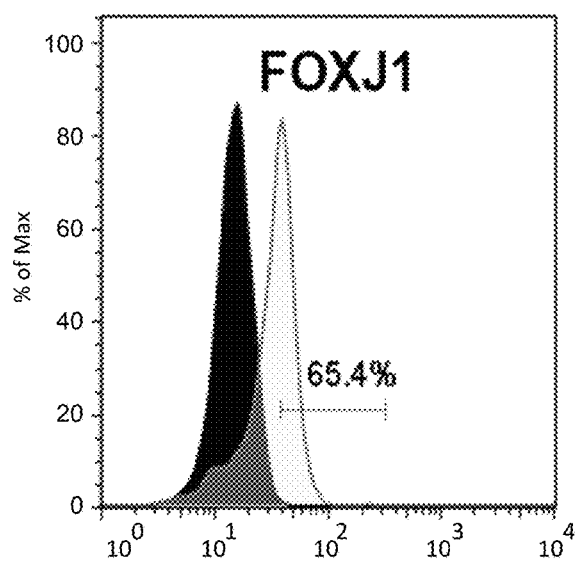
FIG. 12A shows flow cytometric analysis of the cell population derived from iPS cells at day 27 expressing FOXJ1.
Figure 12C:
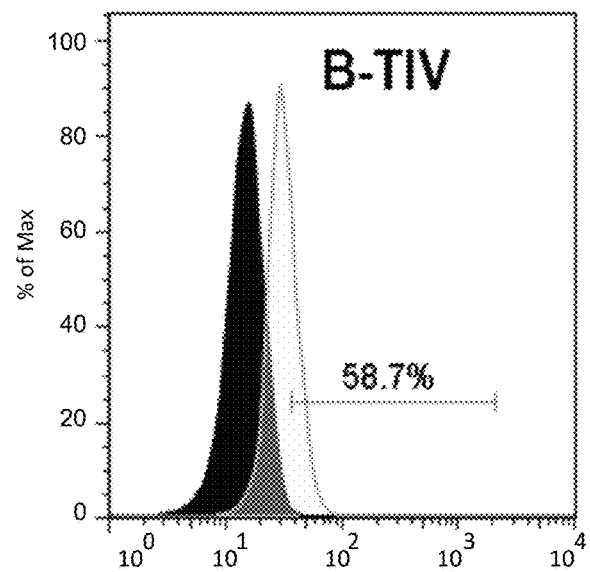
FIG. 12C shows flow cytometric analysis of the cell population derived from iPS cells at day 27 expressing β-tubulin IV.
Figure 12B:
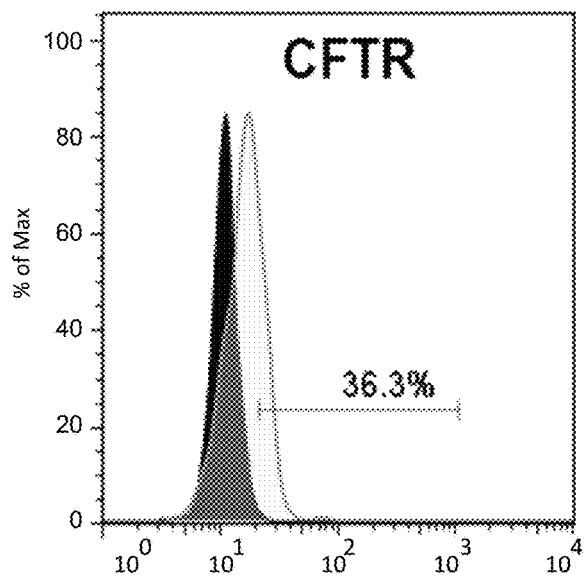
FIG. 12B shows flow cytometric analysis of the cell population derived from iPS cells at day 27 expressing CFTR.
Figure 12D:
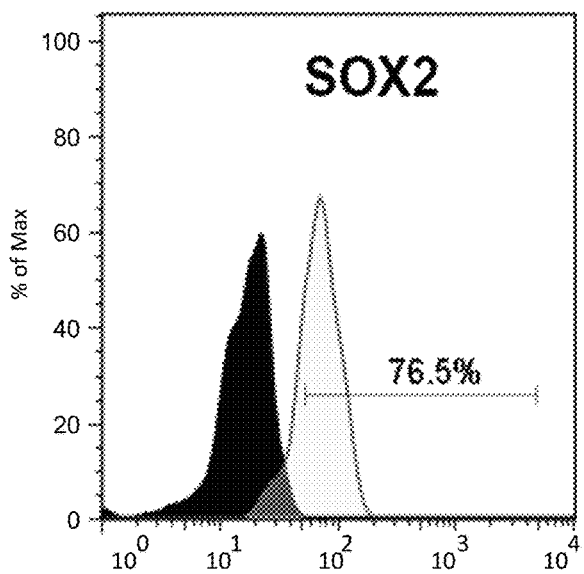
FIG. 12D shows flow cytometric analysis of the cell population derived from iPS cells at day 27 expressing SOX2.

At day 27 flow cytometry revealed the aforementioned growth factors and inhibitor combination induced airway epithelial differentiation when 76% of the cells were positive for the airway cell marker SOX2 (FIGS. 11 and 12D). The percentages of SOX2 positive cells increased from 72% to 92% at day 35. Basal and secretory/ciliated cells are two major epithelial cell lineages in large and small airway compartment. Basal cells (BCs) are pseudostratified epithelia that line the conducting airways of the human lung and previously shown to give rise to other proximal airway lineages. One characteristic of BCs is high expression levels of the transcription factor transformation-related protein 63 (P63) and cytoskeletal proteins, cytokeratins 5 and 14 (KRT5 and KRT14, respectively). These cells proliferate and generate ciliated and secretory cells (Clara cells) in human airway when cultured at the air-liquid interface or in a tracheosphere assay in vitro.

Figure 13E:
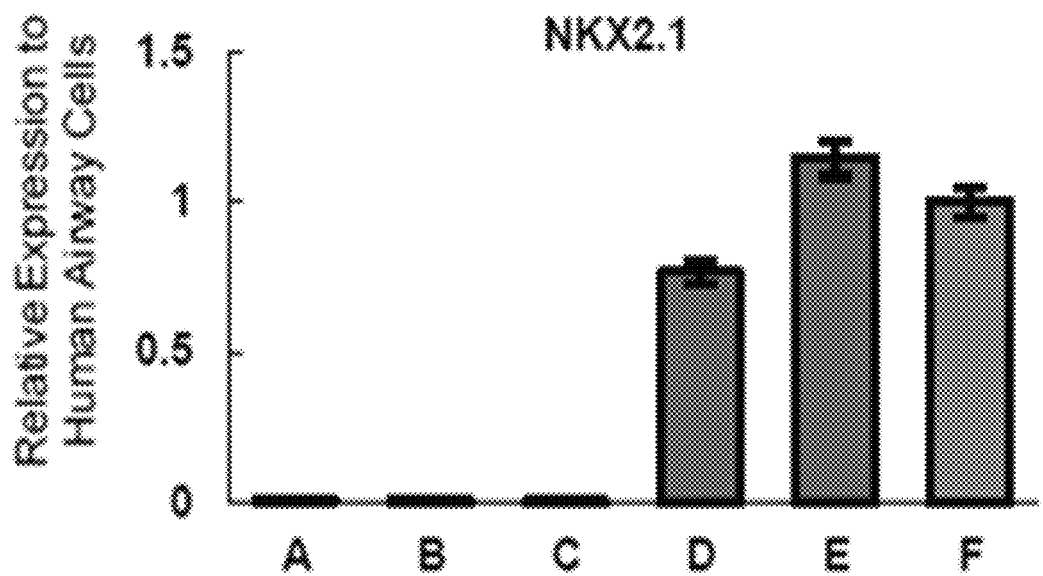
FIG. 13E shows quantitative RT-PCR of NKX2.1 at day 27 results in mature lung airway epithelial cells.
Figure 13F:
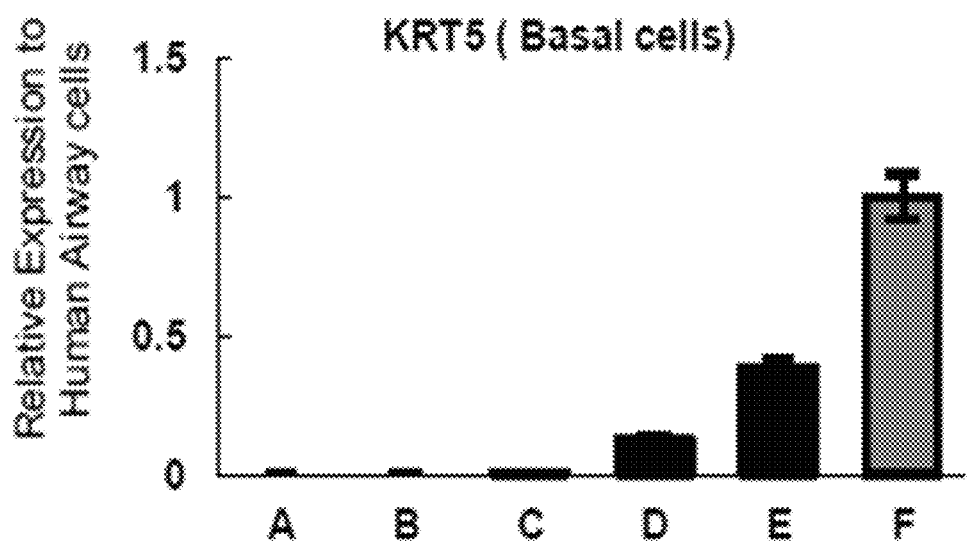
FIG. 13F shows quantitative RT-PCR of KRT5 at day 27 results in mature lung airway epithelial cells.
Figure 14:
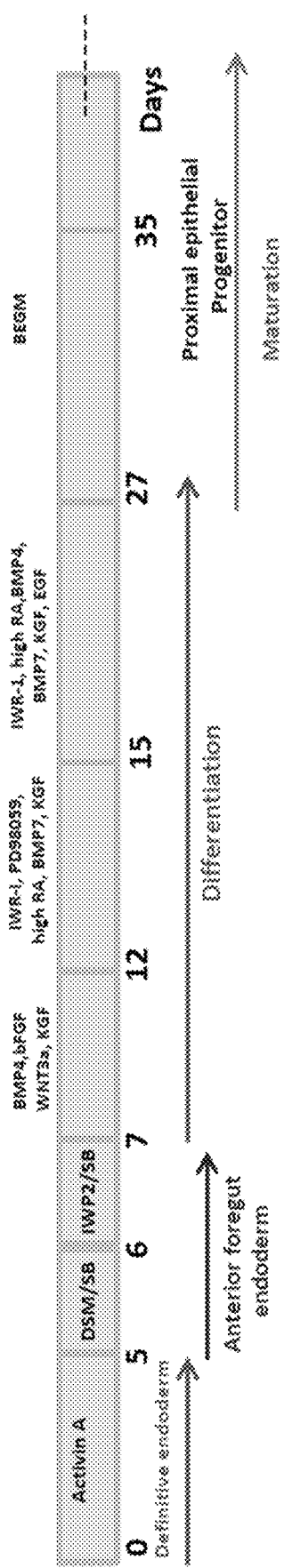
FIG. 14 is a diagram showing at day 35 the maturation of airway epithelial cell differentiation.

At day 27 of differentiation, 64% of cells were positive for KRT5 (FIG. 12F) and over 60% of the cells were P63+ (FIG. 12H), suggesting that the vast majority of the cells were potentially basal cell progenitors. 76% of cells express Clara cell secretory protein (CCSP)(FIG. 12E). Clara-like cells are epithelial secretory cells throughout the proximal to distal axis and have long been thought to act as progenitor cells of the airway. Cystic fibrosis transmembrane conductance regulator (CFTR) is an ABC transporter-class ion channel that transports chloride and thiocyanate ions across epithelial cell membranes. A majority of airway epithelial cells, as well as neuroepithelial cells, express CFTR protein. Flow cytometry analysis revealed that 36% of cells at day 27 were positive for CFTR (FIG. 12B). Up to 65% and 58% of cells were positive for ciliated cell markers, FOXJ1 (FIG. 12A) and β-Tubulin IV (FIG. 12C) respectively suggesting that at least one-third of the cells in the culture have the ciliated CFTR-expressing airway phenotype (FIG. 12B). Only 8% of cells expressed Mucin-5AC, the goblet cell marker (FIG. 12G).

qPCR at day 27 indicated that switching to airway differentiation media resulted in further upregulation of airway genes KRT5 (FIG. 13F), P63, FOXJ1 (FIG. 13B), SOX17, MUC5AC (FIG. 13D) and CFTR (FIG. 13A), while there were lower levels of Mucin5AC, SCGB1A1(CCSP)(FIG. 13C). Other endoderm lineage markers such as AFP (liver), PDX1, TG (Thyroid) and PAX9 (pharyngeal) were not detected at this stage.

ECM proteins have a very specific distribution and assembly pattern in the lung. The complex process of airway epithelial differentiation also involves cell-matrix and cell-cell interaction. Human trachea and airway are mainly composed of collagen I and III in comparison to other ECM protein. Therefore beginning of day 28 cells were transferred onto collagen I/III coated plates in BEGM™ Bronchial Epithelial Cell Growth Medium—from Lonza for another 7 days. Using the modified conditions for human alveolar differentiation, at day 35 the AFE cells were successfully converted into airway epithelial progenitor cells with high efficiency.

Figures 15A, 15B, 15C, 15D, 15E, 15F:
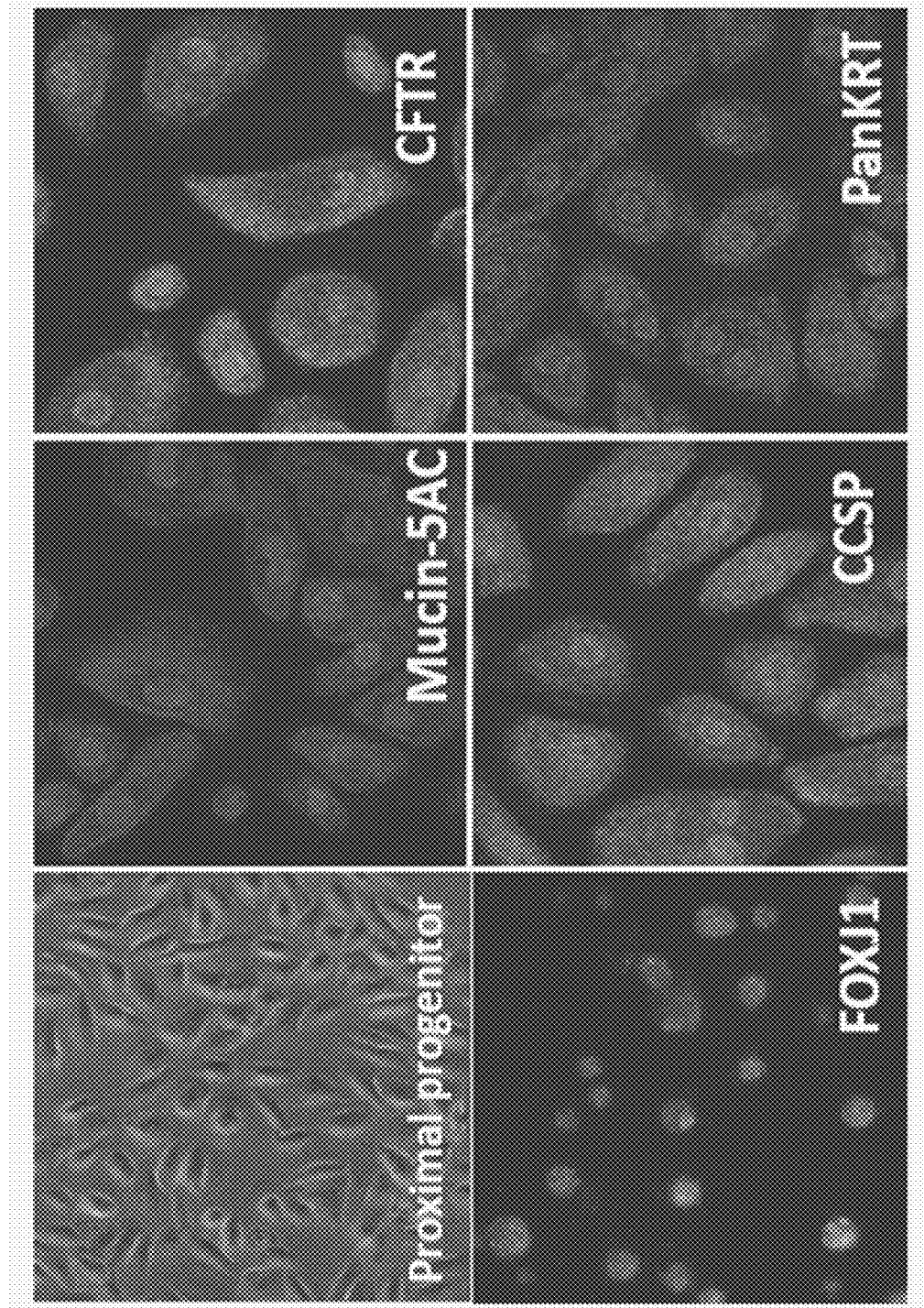
FIG. 15A shows airway epithelial cells stained as proximal progenitors.
FIG. 15B shows airway epithelial cells stained with FOXJ1 antibody.
FIG. 15C shows airway epithelial cells stained with Mucin5AC antibody.
FIG. 15D shows airway epithelial cells stained with CCSP antibody.
FIG. 15E shows airway epithelial cells stained with CFTR antibody.
FIG. 15F shows airway epithelial cells stained with PanKRT antibody.
Figure 16A:
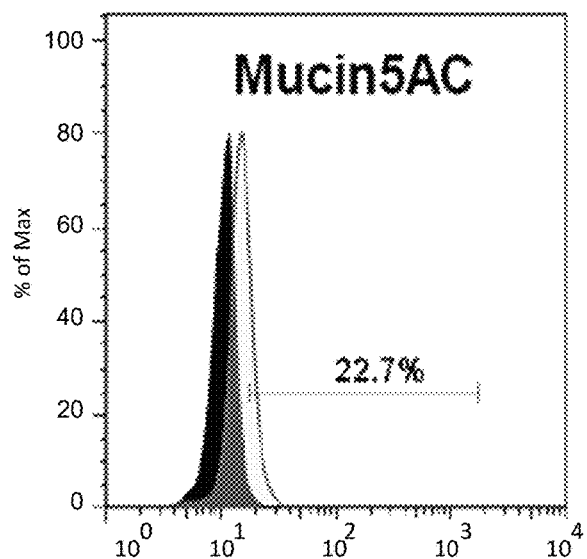
FIG. 16A shows flow cytometric analysis at day 35 for the airway cell marker Mucin5AC.
Figure 16B:
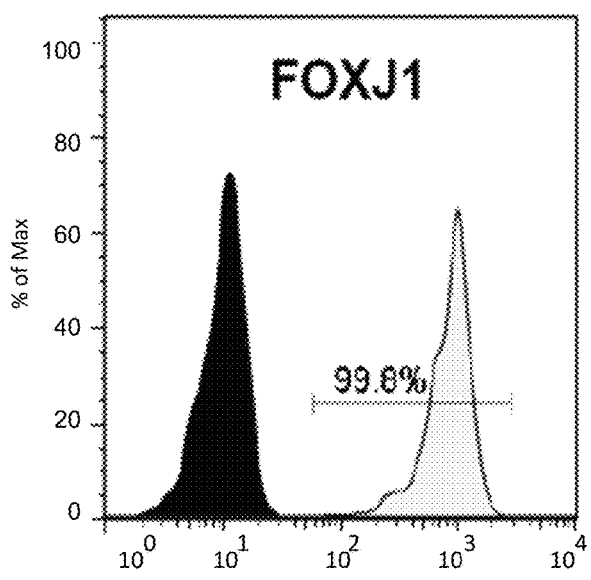
FIG. 16B shows flow cytometric analysis at day 35 for the airway cell marker FOXJ1.
Figure 16C:
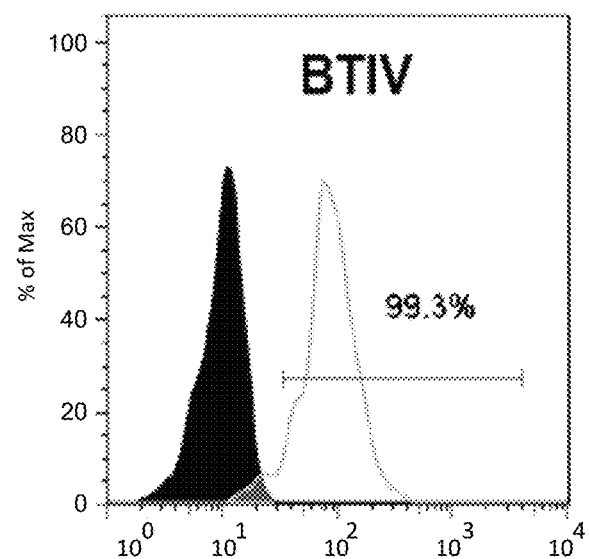
FIG. 16C shows flow cytometric analysis at day 35 for the airway cell marker β-Tubulin IV.
Figure 16D:
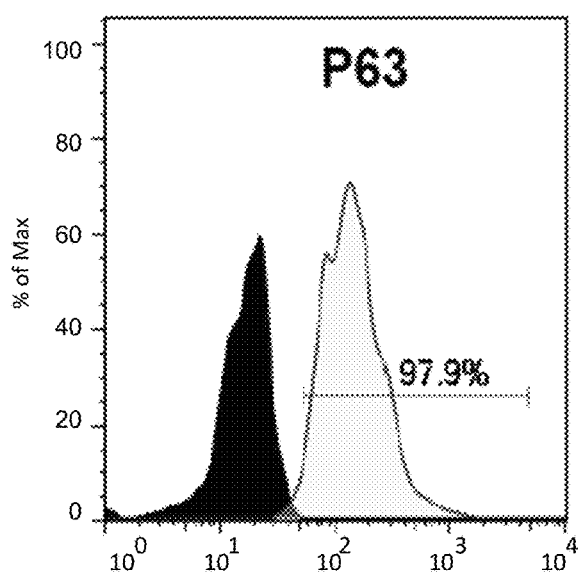
FIG. 16D shows flow cytometric analysis at day 35 for the airway cell marker P63.
Figure 16E:
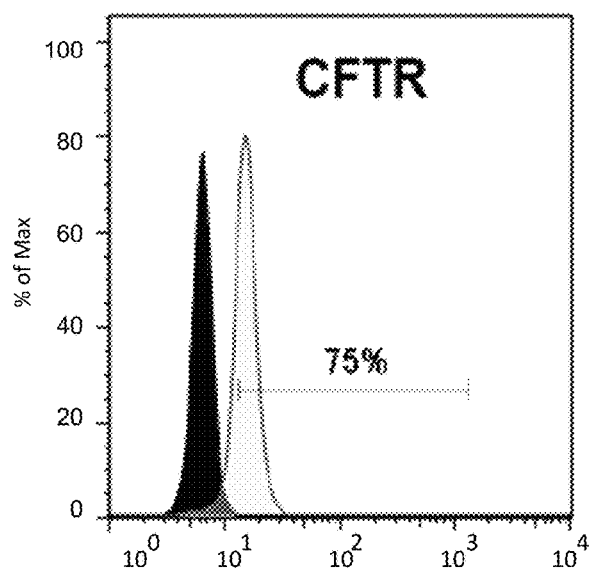
FIG. 16E shows flow cytometric analysis at day 35 for the airway cell marker CFTR.
Figure 16F:
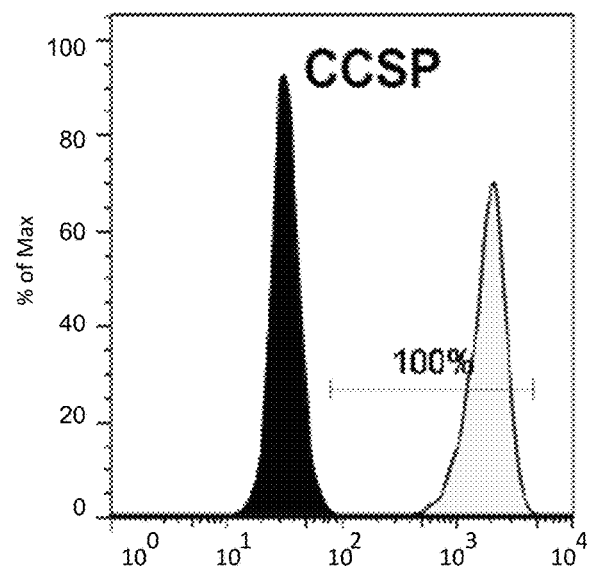
FIG. 16F shows flow cytometric analysis at day 35 for the airway cell marker CCSP.
Figure 16G:
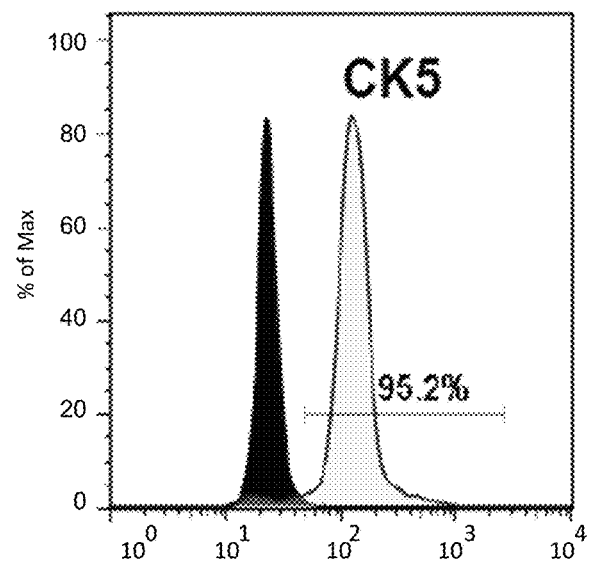
FIG. 16G shows flow cytometric analysis at day 35 for the airway cell marker CK5 or KRT5.
Figure 16H:
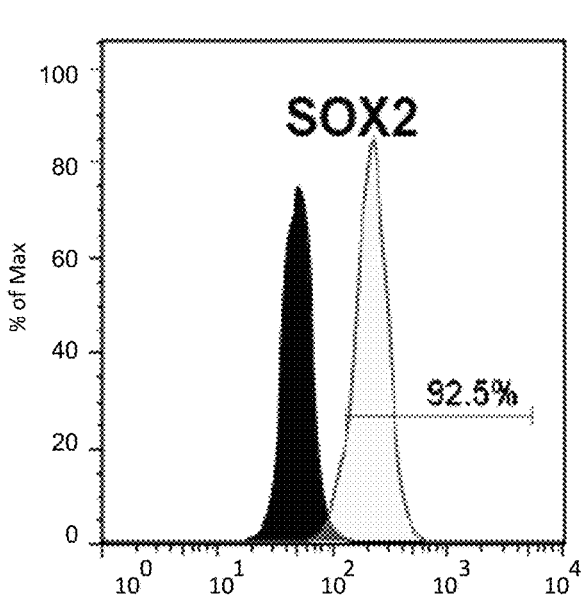
FIG. 16H shows flow cytometric analysis at day 35 for the airway cell marker SOX2.

At day 35 differentiated cells were positively stained for airway epithelial cell markers, CFTR (FIG. 15E), CCSP (FIG. 15D), Mucin5AC (FIG. 15C), FOXJ1 (FIG. 15B) and PanKRT (FIG. 15F). As determined by flow cytometry at day 35, 100% of cells were positive for the airway cell marker, SOX2 (FIG. 16H), and up to 97.5% of cells were positive for P63 (FIG. 16D). Up to 100% of cells expressed CCSP (Clara cells)(FIG. 16F), β-Tubulin IV (FIG. 16C) and FOXJ1 (ciliated cells)(FIG. 16B). 62% and 24% of cells were positive for CFTR (FIG. 16E) and Mucin5AC (FIG. 16A), respectively.

At the end of day 35 the vast majority, 92.2% of the cells, were positive for KRT5 or CK5 while they expressed FOXJ1 and CCSP displaying ciliated and secretory phenotype. This demonstrates that iPS cell-derived airway cells still have multipotent potential at this stage. It is possible that the airway progenitors or basal cells maintained expression of basal cell markers, KRT5 and P63 when they are undergoing differentiation to other proximal cells such as Clara cells and ciliated cells. Gomperts et al demonstrated in organoid assays that Clara cells express FOXJ1, had a ciliated phenotype, as well as contained cells that expressed Muc5AC, CCSP and keratin 5.

Quantitative RT-PCR at day 35 revealed that CK5 or KRT5 (FIG. 17A), SCGB1A1 (CCSP)(FIG. 17E), CFTR (FIG. 17B), P63 (FIG. 17D), FOXJ1 (FIG. 17F) and Mucin-5AC (FIG. 17G) were highly expressed in iPS derived airway epithelial cells, with expression levels comparable to freshly isolated human airway cells. These genes were not detectable in undifferentiated iPS, DE, AFE cells.

Figure 18:
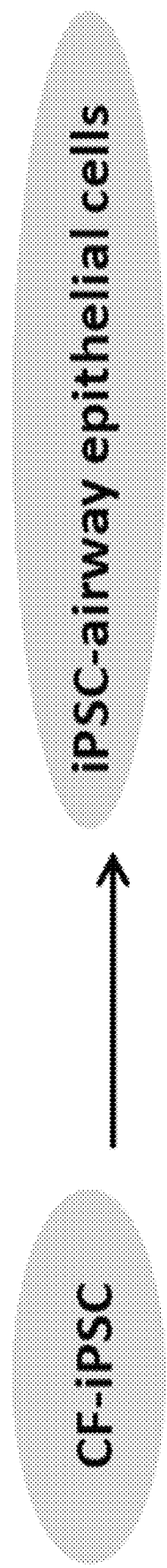
FIG. 18 diagrams a stepwise differentiation approach to generate lung airway progenitors from CF disease-specific human iPS cells.
Figures 21C, 21D:
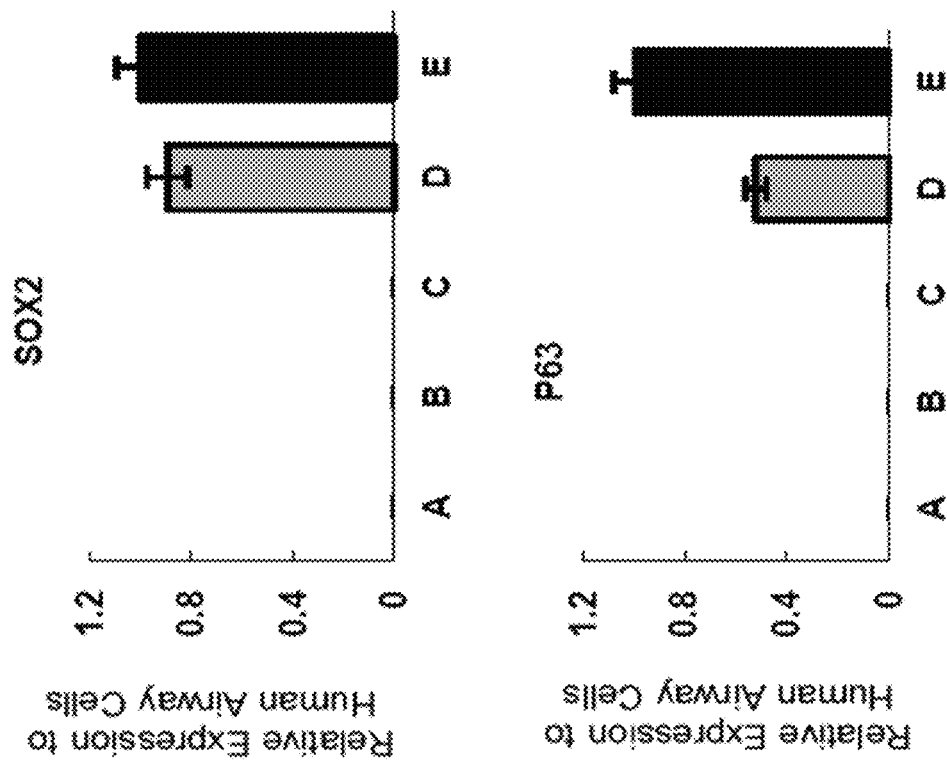
FIG. 21C shows quantitative RT-PCR of SOX2 in airway epithelial cells derived from CF disease-specific human iPS cells.
FIG. 21D shows quantitative RT-PCR of P63 in airway epithelial cells derived from CF disease-specific human iPS cells.
Figures 21A, 21B:
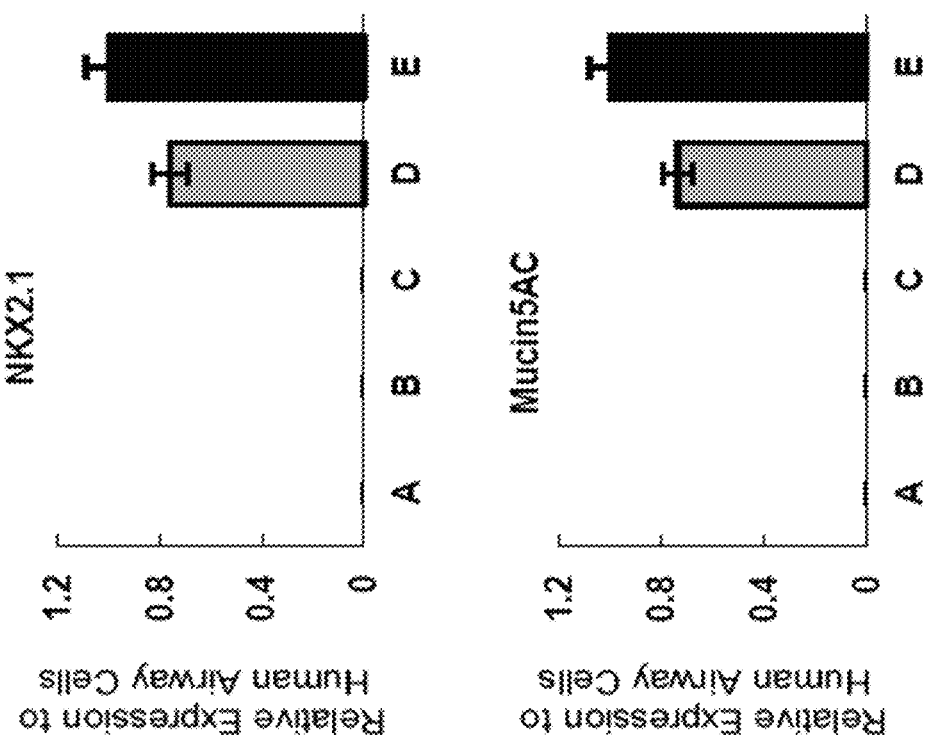
FIG. 21A shows quantitative RT-PCR of NKX2.1 in airway epithelial cells derived from CF disease-specific human iPS cells.
FIG. 21B shows quantitative RT-PCR of Mucin5AC in airway epithelial cells derived from CF disease-specific human iPS cells.
Figure 21E:
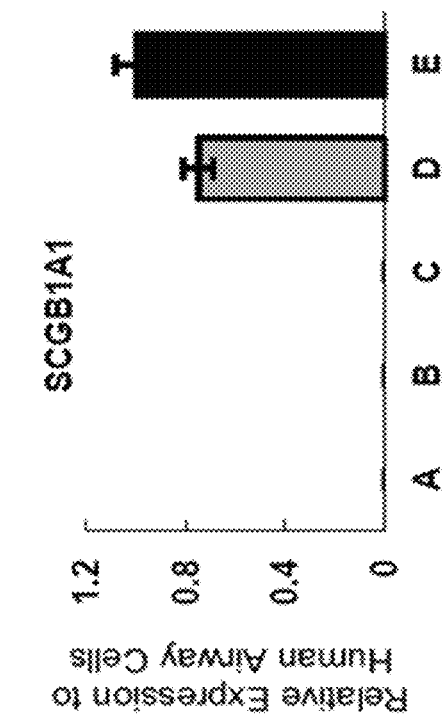
FIG. 21E shows quantitative RT-PCR of SCGB1A1 or CCSP in airway epithelial cells derived from CF disease-specific human iPS cells.
Figure 21G:
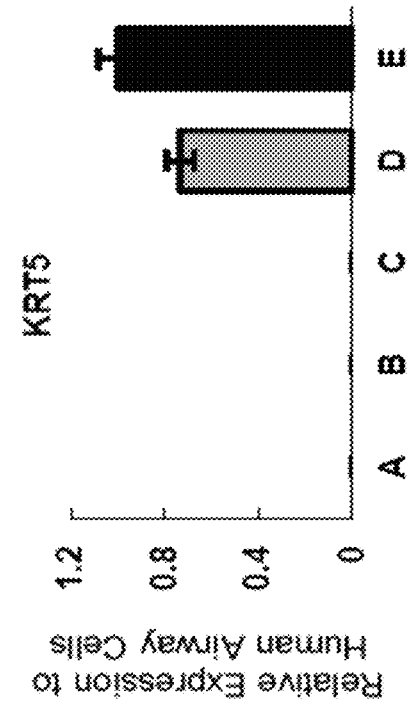
FIG. 21G shows quantitative RT-PCR of KRT5 in airway epithelial cells derived from CF disease-specific human iPS cells.
Figure 21F:
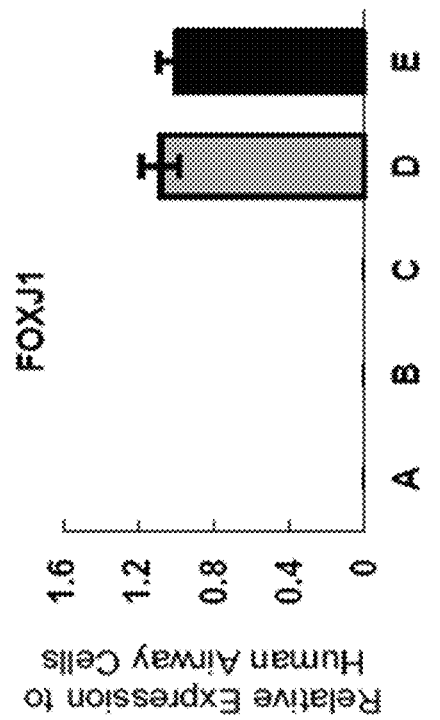
FIG. 21F shows quantitative RT-PCR of FOXJ1 in airway epithelial cells derived from CF disease-specific human iPS cells.
Figure 21H:
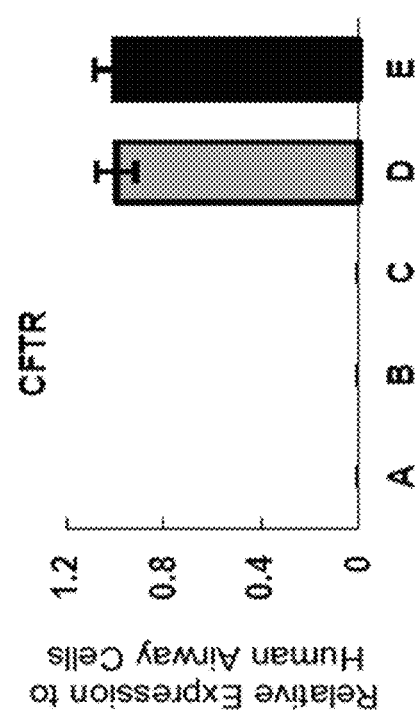
FIG. 21H shows quantitative RT-PCR of CFTR in airway epithelial cells derived from CF disease-specific human iPS cells.

Next, a similar stepwise differentiation approach was examined to generate lung airway progenitors from CF disease-specific human iPS cells (FIG. 18). Interestingly, CF-iPS cell clones yielded similar results and had similar efficiency to differentiate toward DE, AFE, airway epithelial cells, suggesting this protocol can be generalized to other iPS cell lines from other sources (FIGS. 19A-19D showing cell staining, FIGS. 20A-20H showing flow cytometric analysis and FIGS. 21A-21H showing quantitative RT-PCR results).

Immunostaining analysis also showed that the airway progenitor cell population derived from iPSCs were able to develop into lung organoid structures in Matrigel. The structures were positive for airway markers, P63 (FIG. 22A) and NKX2.1 (FIG. 22B).

Developing advanced technologies for the ex vivo assembly of functional alveolar tissue for implantation into the human body is one of the challenging tasks facing tissue engineers. Recent advances in differentiating of ESCs and iPS cells to pulmonary epithelial cells or precursors have suggested a promising therapeutic strategy using stem-cell derived epithelial cells for lung engineering.

In the present study a highly efficient method was developed for the directed differentiation of iPS cells to functional conducting airway epithelial cells, which can be used for recellularization of decellularized lung scaffolds and which ultimately may provide an autologous graft for lung transplantation. Notably, this method of directed differentiation was broadly applicable to several pluripotent cell lines (human iPS cells clone C1, reprogrammed from fetal lung fibroblasts and CF-iPS cell, reprogrammed from dermal fibroblasts). Both iPS cell clones yield similar results and had similar efficiency to differentiate toward DE, AFE and different types of airway cells, suggesting this protocol can be generalized to other iPS cell lines from other sources. Most efforts in the differentiation of iPS cell to alveolar epithelium are focused on the generation of type II epithelial cells and few studies have targeted the differentiation of airway epithelium. In all published reports the efficacy was low and the expression of airway marker appears to be stochastic. In heterogeneous cultures of differentiating ESCs and iPS cells with low efficacy there is a risk of remaining undifferentiated pluripotent stem cells within the populations which can carry a significant risk of teratoma formation after transplantation. No matter which stem cell type is used for differentiation, challenges remain in lung engineering particularly in the generation of large quantities of well-differentiated cells. In previous reports the differentiated airway cells from iPS cells have been difficult to expand. Unlike isolated airway cells, however, iPS cell-derived airway cells in this study are capable of proliferating for several passages without losing airway epithelial cell-associated markers, such as CCSP, P63, FOXJ1, CFTR and mucin-5AC, and can be used to generate tens of millions of cells with which to seed the acellular matrix scaffold. The ability to "scale up" a progenitor population will be particularly valuable when translating these technologies for use in producing tissue engineered human lung tissues, using autologous iPS cell derived cells.

Moreover, providing a supply of defined transplantable cells that allow treatment of patients afflicted with genetic and degenerative disorders is a major goal of human cell therapy. In certain lung diseases, such as cystic fibrosis, transplantation of adult lung stem and progenitor cells or alveolar cells isolated from human lung is emerging as a new therapeutic approach to restore normal lung functions in patients. However, this approach is limited by a scarcity of human alveolar cells and, more importantly, a lack of engraftment of such cells in vivo in injured lungs.

Airway epithelial cells or lung epithelial precursors derived from iPS cells provide a promising therapeutic strategy using stem-cell based inhaled therapies to replace native lung epithelial cells and reconstitute healthy pulmonary epithelia in patients.

Moreover, the development of new drugs is costly and is resource intensive. iPS derived airway epithelial cells are potentially very valuable for pharmaceutical development, spanning from use as tools in early target studies and safety assessments, as well as screening models to find new chemical entities. The iPS derived airway epithelial cells can be useful for testing drugs on the pathology of a lung tissue. In addition, the iPS derived airway epithelial cells can be used to examine the effects of particular delivery vehicles for therapeutic agents on the pathology of lung tissue, for example, to compare the effects of the same agent administered via different delivery systems, or simply to assess whether a delivery vehicle itself (e.g. a viral vector vs non-viral) is capable of affecting lung pathology.

Direct differentiation of iPS cells on feeder layers or Matrigel to the definitive endoderm stage was used instead of the embroid body method. Direct differentiation towards DE yielded populations of high purity when compared to the EB method. This was largely because in the embroid body, even in the presence of activin A, cells remained from two other embryonic germ layers, the mesoderm and ectoderm.

To induce definitive endoderm, iPS cells were cultured in RPMI 1640 medium without serum supplemented with 100 ng/ml activin A for 48 hours. Then, 1xB27 supplement, 0.5 mM sodium were butyrate was added into the same medium and iPS cells were cultured in this medium for another 3 days. In previously established published protocols, cells were cultured in medium containing activin A for 4 days instead of 5 days. 1xB27 supplement provided low serum condition. These cells also showed a uniform morphology in the presence of sodium butyrate.

In other protocols, investigators have mostly used no serum media or defined media. In contrast, the modified protocol described herein resulted in IPS derived cell populations at day 5 that expressed a high percentage of markers associated with this germ layer. The population of cells were 89% of cells were positive for c-kit, 91% positive for SOX17, 93% positive for FOXA2, and 88% of the cells expressed the endoderm surface marker CXCR4 in clone C1.

To differentiate definitive endoderm to anterior foregut endoderm the DE cells were cultured in IMDM containing 5% FBS and Dorsomorphin/SB141524. Other protocols used other basal media instead of IMDM and the others used either no serum media or defined media.

To control differentiation from anterior foregut endoderm to conducting airway cells, growth factors and extracellar protein matrix were the focus. In the differentiation methods described herein, EGF, KGF and BMP7, BMP4, IWR-1 (WNT3a inhibitor) and high retinoic acid in IMDM with 10% FBS were chosen. This differentiation cocktail has not been used in previous reports.

The methods described herein mimic lung development during embryogenesis using extracellar matrix proteins that exist in the lung (these include collagens, laminin, fibronectin, tenascin, elastin, and a number of proteoglycans and glycosaminoglycans) and a combination of growth factors that play a central role in lung development and regeneration. iPS cells were first differentiated towards definitive endoderm (DE) and then cultured on ECM coated surfaces. The discovery of the differentiation methods described herein are the first to use ECM coated surfaces for airway epithelial cell differentiation along with growth factors in human iPS cells for tissue-specific differentiation.

The complex process of airway epithelial differentiation also involves cell-matrix and cell-cell interaction. Human trachea and airway are composed mainly of collagen I and III. Therefore, beginning on day 28, cells were transferred onto collagen I/III coated plates in BEGM™ Bronchial Epithelial Cell Growth Medium—from Lonza for another 5 days. This study is one of the first to use collagen VIII mix coated surface for airway epithelial differentiation from iPS cells.

It was unexpected to discover that human pluripotent stem cells can be directed to differentiate in vitro into conducting airway epithelium with high efficacy. Using the methods described herein for human airway differentiation, at day 35, the AFE cells were successfully converted into airway epithelial progenitor cells with high efficiency. As determined by flow cytometry at day 35, about 100% of cells were positive for the airway cell marker, SOX2, and up to about 97.5% of cells were positive for P63. Additionally, up to about 100% of the cells expressed CCSP (Clara cells) and β-Tubulin IV and FOXJ1(ciliated cells). About 62% and 24% of cells were positive for CFTR and Mucin5AC, respectively.

At the end of day 35 the vast majority, about 92.2%, of the cells were positive for KRT5, while they expressed FOXJ1 and CCSP showing ciliated and secretory phenotype. Quantitative RT-PCR also revealed that CK5, SCGB1a1 (CCSP), CFTR, P63, FOXJ1 and Mucin-5AC were highly expressed in iPS derived airway epithelial cells, with the relative levels compared to freshly isolated human airway cells.

Unlike isolated airway cells, the iPS cell-derived airway cells described herein are capable of proliferating for several passages without losing airway epithelial cell-associated markers, such as CCSP, P63, FOXJ1, CFTR and mucin-5AC. This makes it possible to generae tens of millions of cells for further purposes, such as seeding the acellular matrix scaffolds for making engineered lung tissues.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An airway epithelial cell derived from an induced pluripotent stem (iPS) cell characterized by:
    expression of airway cell surface markers, wherein the airway cell surface markers comprise Clara cell secretory protein (CCSP), cytokeratin 5 (KRT5), and FOXJ1; and
    an ability to proliferate in culture for at least about 30 days without loss of the airway cell surface markers;
    wherein the iPS cell is cultured in the absence of serum to induce differentiation into a definitive endoderm (DE) cell;
    wherein the DE cell is cultured in the presence of serum to induce differentiation into an anterior foregut endoderm (AFE) cell; and
    wherein the AFE cell is cultured in the presence of serum, a cytokine cocktail that inhibits WNT pathway, and at least 0.5 µM retinoic acid to induce differentiation of the AFE cell into the airway epithelial cell.

2. The airway epithelial cell of claim 1, wherein the airway epithelial cell is ciliated.

3. The airway epithelial cell of claim 1, further characterized by expression of cystic fibrosis transmembrane conductance regulator protein (CFTR).

4. The airway epithelial cell of claim 1, further characterized by expression of at least one of β-tubulin IV, mucin-5AC, and P63.

5. The airway epithelial cell of claim 1, wherein the airway cell surface markers are expressed at a level comparable to that expressed on freshly isolated human airway cells.

6. The airway epithelial cell of claim 1, wherein the airway epithelial cell is derived from a cystic fibrosis human iPS cell.

7. The airway epithelial cell of claim 1, wherein the cytokine cocktail comprises epidermal growth factor (EGF), keratinocyte growth factor (KGF), bone morphogenic protein 7 (BMP7), bone morphogenic protein 4 (BMP4), and IWR-1.

* * * * *